US011367180B2

(12) United States Patent
Coudray et al.

(10) Patent No.: US 11,367,180 B2
(45) Date of Patent: Jun. 21, 2022

(54) CLASSIFICATION AND MUTATION PREDICTION FROM HISTOPATHOLOGY IMAGES USING DEEP LEARNING

(71) Applicant: NEW YORK UNIVERSITY, New York, NY (US)

(72) Inventors: Nicolas Coudray, New York, NY (US); Paolo Santiago Ocampo, Brooklyn, NY (US); Andre L. Moreira, New York, NY (US); Narges Razavian, New York, NY (US); Aristotelis Tsirigos, Hicksville, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 16/711,199

(22) Filed: Dec. 11, 2019

(65) Prior Publication Data

US 2020/0184643 A1 Jun. 11, 2020

Related U.S. Application Data

(60) Provisional application No. 62/778,108, filed on Dec. 11, 2018.

(51) Int. Cl.
| | |
|---|---|
| *G06K 9/00* | (2022.01) |
| *G06T 7/00* | (2017.01) |
| *G01N 33/574* | (2006.01) |
| *G06V 20/69* | (2022.01) |

(52) U.S. Cl.
CPC ..... *G06T 7/0012* (2013.01); *G01N 33/57423* (2013.01); *G06V 20/698* (2022.01); *C12Q 2600/156* (2013.01); *G06T 2207/20084* (2013.01); *G06T 2207/30061* (2013.01); *G06T 2207/30096* (2013.01)

(58) Field of Classification Search
None
See application file for complete search history.

(56) References Cited

U.S. PATENT DOCUMENTS 10,832,406 B2 * 11/2020 Yu ..................... G06K 9/00147

OTHER PUBLICATIONS

Coudray et al., "Classification and mutation prediction from non-small cell lung cancer histopathology images using deep learning", published and tweeted about on Oct. 3, 2017 (Year: 2017).*
Saltz et al., "Spatial organization and molecular correlation of tumor-infiltrating lymphocytes using deep learning on pathology images", Apr. 3, 2018 (Year: 2018).*
Amachika, T., et al., "Diagnostic relevance of overexpressed mRNA of novel oncogene with kinase-domain (NOK) in lung cancers", Lung Cancer, 2007, 56(3):337-340.

(Continued)

*Primary Examiner* — Soo Jin Park
(74) *Attorney, Agent, or Firm* — Foley & Lardner LLP

(57) ABSTRACT

Systems and methods for classification and mutation prediction from histopathology images using deep learning. In particular, the examples described herein utilize lung cancer as an example, in particular adenocarcinoma (LUAD) and squamous cell carcinoma (LUSC) as two subtypes of lung cancer to identify and distinguish between.

25 Claims, 16 Drawing Sheets

(56) References Cited

OTHER PUBLICATIONS

Anthimopoulos, M., et al., "Lung Pattern Classification for Interstitial Lung Diseases Using a Deep Convolutional Neural Network", IEEE Transactions on Medical Imaging, May 2016, 35(5):1207-1216.
Bhattacharjee, A., et al., "Classification of human lung carcinomas by mRNA expression profiling reveals distinct adenocarcinoma subclasses", PNAS, Nov. 20, 2001, 98(24):13790-13795.
Blumenthal, G.M., et al., "Oncology Drug Approvals: Evaluating Endpoints and Evidence in an Era of Breakthrough Therapies", The Oncologist, 2017, 22(7):762-767.
Bonner, et al., "Laser Capture Microdissection: Molecular Analysis of Tissue", Science, Nov. 21, 1997, 278:1481-1483.
Chan, B.A., et al., "Targeted therapy for non-small cell lung cancer: current standards and the promise of the future", Transl Lung Cancer Res, 2015, 4(1):36-54.
Charkiewicz, R., et al., "Gene Expression Signature Differentiates Histology but not Progression Status of Early-Stage NSCLC1", Translational Oncology, Jun. 2017, 10(3):450-458.
Cheng, J-Z., et al., "Computer-Aided Diagnosis with Deep Learning Architecture: Applications to Breast Lesions in US Images and Pulmonary Nodules in CT Scans", Scientific Reports, 2016, 6:24454, 13 pages.
Cheng, M., et al., "Diagnostic utility of LunX mRNA in peripheral blood and pleural fluid in patients with primary non-small cell lung cancer", BMC Cancer, 2008, 8:156, 12 pages.
Coudray, N., et al., "Classification and mutation prediction from non-small cell lung cancer histopathology images using deep learning", Nature Medicine, Oct. 2018, 24:1559-1567.
Cruz-Roa, A., et al., "Accurate and reproducible invasive breast cancer detection in whole-slide images: A Deep Learning approach for quantifying tumor extent", Scientific Reports, 2017, 7:46450, 14 pages.
Cuezva, J.M., et al., "The bioenergetic signature of lung adenocarcinomas is a molecular marker of cancer diagnosis and prognosis", Carcinogenesis, 2004, 25(7):1157-1163.
Donovan, M.J., et al., "Implementation of a Precision Pathology Program Focused on Oncology-Based Prognostic and Predictive Outcomes", Molecular Diagnosis & Therapy, 2017, 21(2):115-123.
Donovan, M.J., et al., "A systems pathology model for predicting overall survival in patients with refractory, advanced non-small-cell lung cancer treated with gefitinib", European Journal of Cancer, 2009, 45(8):1518-1526.
Du, Y-Z., et al., "The Diagnostic Value of Circulating Stanniocalcin-1 mRNA in Non-Small Cell Lung Cancer", Journal of Surgical Oncology, 2011, 104(7):836-840.
Esteva, A., et al., "Dermatologist-level classification of skin cancer with deep neural networks", Nature, Feb. 2, 2017, 542:115-118.
Girard, L., et al., "An Expression Signature as an Aid to the Histologic Classification of Non-Small Cell Lung Cancer", Clinical Cancer Research, Oct. 1, 2016, 22(19):4880-4889.
Goode, A., et al., "OpenSlide: A vendor-neutral software foundation for digital pathology", Journal of Pathology Informatics, 2013, 4(27), 8 pages.
Greenspan, H., et al., "Deep Learning in Medical Imaging: Overview and Future Promise of an Exciting New Technique", IEEE Transactions on Medical Imaging, May 2016, 35(5):1153-1159.
Grilley-Olson, J.E., et al., "Validation of Interobserver Agreement in Lung Cancer Assessment: Hematoxylin-Eosin Diagnostic Reproducibility for Non-Small Cell Lung Cancer: The 2004 World Health Organization Classification and Therapeutically Relevant Subsets", Archives of Pathology and Laboratory Medicine, Jan. 2013, 137(1):32-40.
Grossman, R.L., et al., "Toward a Shared Vision for Cancer Genomic Data", The New England Journal of Medicine, Sep. 22, 2016, 375:1109-1112.
Gulshan, V., et al., "Development and Validation of a Deep Learning Algorithm for Detection of Diabetic Retinopathy in Retinal Fundus Photographs", JAMA, Dec. 13, 2016, 316(22):2402-2410.
Hanley, J.A., et al., "The Meaning and Use of the Area under a Receiver Operating Characteristic (ROC) Curve", Radiology, Apr. 1982, 143(1):29-36.
Hershey, S., et al., "CNN Architectures for Large-Scale Audio Classification", IEEE International Conference on Acoustics, Speech and Signal Processing, 2017, pp. 131-135.
Hinton, G.E., et al., "A Fast Learning Algorithm for Deep Belief Nets", Neural Computation, 2006, 18(7):1527-1554.
Hou, J., et al., "Gene Expression-Based Classification of Non-Small Cell Lung Carcinomas and Survival Prediction", PLoS ONE, Apr. 2010, 5(4):e10312, 12 pages.
Janne, P.A., et al., "Selumetinib plus docetaxel for KRAS-mutant advanced non-small-cell lung cancer: a randomised, multicentre, placebo-controlled, phase 2 study", Lancet Oncol, 2013, 14(1):38-47.
Kandoth, C., et al., "Mutational landscape and significance across 12 major cancer types", Nature, Oct. 17, 2013, 502:333-339.
Khosravi, P., et al., "Deep Convolutional Neural Networks Enable Discrimination of Heterogeneous Digital Pathology Images", EBioMedicine, 2018, 27:317-328.
Liaw, A., et al., "Classification and Regression by randomForest", R News, Dec. 2002, 2/3:18-22.
Lin, M., et al., "Network in Network", Cornell University Computer Science, Neural and Evolutionary Computing, arXiv:1312.4400, Mar. 4, 2014, 10 pages.
Luo, X., et al., "Comprehensive Computational Pathological Image Analysis Predicts Lung Cancer Prognosis", Journal of Thoracic Oncology, 12(3):501-509.
Makowski, L., et al., "Role of LKB1 in lung cancer development", British Journal of Cancer, 2008, 99:683-688.
Mishra, R., et al., "Histopathological Diagnosis for Viable and Non-viable Tumor Prediction for Osteosarcoma Using Convolutional Neural Network", in Z. Cai et al. (Eds.), International Symposium on Bioinformatics Research and Applications, 2017, pp. 12-23, Springer International Publishing AG.
Mogi, A., et al., "TP53 Mutations in Nonsmall Cell Lung Cancer", Journal of Biomedicine and Biotechnology, 2011, 583929, 9 pages.
Morris, L.G.T., et al., "Recurrent somatic mutation of FAT1 in multiple human cancers leads to aberrant Wnt activation", Nature Genetics, 2013, 45:253-261.
Parums, D.V., "Current Status of Targeted Therapy in Non-Small Cell Lung Cancer", Drugs of Today, 2014, 50(7):503-525.
Perez-Soler, R., et al., "Determinants of Tumor Response and Survival With Erlotinib in Patients With Non—Small-Cell Lung Cancer", Journal of Clinical Oncology, Aug. 15, 2004, 22(16):3238-3247.
Qaiser, T., et al., "Tumor Segmentation in Whole Slide Images Using Persistent Homology and Deep Convolutional Features", 21st Annual Conference on Medical Image Understanding and Analysis, 2017, pp. 320-329.
Sanchez-Cespedes, M., et al., "Inactivation of LKB1/STK11 Is a Common Event in Adenocarcinomas of the Lung", Cancer Research, Jul. 1, 2002, 62(13):3659-3662.
Schmidhuber, J., "Deep learning in neural networks: An overview", Neural Networks, 2015, 61:85-117.
Shackelford, D.B., et al., "LKB1 Inactivation Dictates Therapeutic Response of Non-Small Cell Lung Cancer to the Metabolism Drug Phenformin", Cancer Cell, Feb. 11, 2013, 23(2):143-158.
Shen, D., et al., "Deep Learning in Medical Image Analysis", Annual Review of Biomedical Engineering, Jun. 21, 2017, 19:221-248.
Sheu, C-C., et al., "Combined Detection of CEA, CK-19 and c-met mRNAs in Peripheral Blood: A Highly Sensitive Panel for Potential Molecular Diagnosis of Non-Small Cell Lung Cancer", Oncology, 2006, 70:203-211.
Shum, E., et al., "Investigational therapies for squamous cell lung cancer: from animal studies to phase II trials", Expert Opinion on Investigational Drugs, 2017, 26(4):415-426.

(56) References Cited

OTHER PUBLICATIONS

Sirinukunwattana, K., et al., "Locality Sensitive Deep Learning for Detection and Classification of Nuclei in Routine Colon Cancer Histology Images", IEEE Transactions on Medical Imaging, May 2016, 35(5):1196-1206.

Szegedy, C., et al., "Going Deeper With Convolutions", IEEE Conference on Computer Vision and Pattern Recognition, 2015, pp. 1-9.

Szegedy, C., et al., "Rethinking the Inception Architecture for Computer Vision", IEEE Conference on Computer Vision and Pattern Recognition, 2016, pp. 2818-2826.

Terra, S., et al., "Molecular characterization of pulmonary sarcomatoid carcinoma: analysis of 33 cases", Modern Pathology, 2016, 29:824-831.

Terry, J., et al., "Optimal Immunohistochemical Markers for Distinguishing Lung Adenocarcinomas From Squamous Cell Carcinomas in Small Tumor Samples", The American Journal of Surgical Pathology, Dec. 2010, 34(12):1805-1811.

The Cancer Genome Atlas Research Network, "Comprehensive genomic characterization of head and neck squamous cell carcinomas", Nature, Jan. 29, 2015, 517:576-582.

The Cancer Genome Atlas Research Network, "Comprehensive genomic characterization of squamous cell lung cancers", Nature, Sep. 27, 2012, 489:519-525.

The Cancer Genome Atlas Research Network, "Comprehensive molecular profiling of lung adenocarcinoma", Nature, Jul. 31, 2014, 511:543-550.

Travis, W.D., et al., "International Association for the Study of Lung Cancer/American Thoracic Society/European Respiratory Society International Multidisciplinary Classification of Lung Adenocarcinoma", Journal of Thoracic Oncology, Feb. 2011, 6(2):244-285.

Van Der Maaten, L., "Accelerating t-SNE using Tree-Based Algorithms", Journal of Machine Learning Research, 2014, 15:3221-3245.

Wang, D., et al., "Deep Learning for Identifying Metastatic Breast Cancer", Cornell University Quantitative Biology, Quantitative Methods, arXiv:1606.05718, Jun. 18, 2016, 6 pages.

Wilkerson, M.D., et al., "Prediction of Lung Cancer Histological Types by RT-qPCR Gene Expression in FFPE Specimens", The Journal of Molecular Diagnostics, Jul. 2013, 15(4):485-497.

Yu, K-H., et al., "Predicting non-small cell lung cancer prognosis by fully automated microscopic pathology image features", Nature Communications, 2016, 7:2474, 10 pages.

Zeiler, M.D., et al., "Visualizing and Understanding Convolutional Networks", European Conference on Computer Vision, 2014, pp. 818-833.

\* cited by examiner

CLASSIFICATION AND MUTATION PREDICTION FROM HISTOPATHOLOGY IMAGES USING DEEP LEARNING

CROSS-REFERENCE TO RELATED APPLICATIONS

The present application claims the benefit of priority under 35 U.S.C. § 119(e) to U.S. Provisional Application No. 62/778,108 filed Dec. 11, 2018 the entire contents of which are incorporated herein by reference.

GOVERNMENT RIGHTS

This invention was made with government support under Grant No. P30CA016087, a Cancer Center Support Grant awarded to New York University School of Medicine. The government has certain rights in the invention.

BACKGROUND

Visual inspection of histopathology slides is one of the main methods used by pathologists to assess the stage, type and subtype of tumors. As just one example of common tumors, lung cancers are frequently diagnosed by visual inspection. The specific type or subtype of lung cancer present in a patient may dramatically impact the course of treatment. Classification of cancer type is a key diagnostic process because the available treatment options, including conventional chemotherapy and, more recently, targeted therapies, differ for different cancers. Therefore, it is critical to be able to identify, accurately and quickly, the particular cancer in a patient.

Adenocarcinoma (LUAD) and squamous cell carcinoma (LUSC) are the most prevalent subtypes of lung cancer, and their distinction requires visual inspection by an experienced pathologist. According to the American Cancer Society and the Cancer Statistics Center (see URLs), over 150,000 patients with lung cancer succumb to the disease each year (154,050 expected for 2018), while another 200,000 new cases are diagnosed on a yearly basis (234,030 expected for 2018). It is one of the most widely spread cancers in the world because of not only smoking, but also exposure to toxic chemicals like radon, asbestos and arsenic. LUAD and LUSC are the two most prevalent types of non-small cell lung cancer, and each is associated with discrete treatment guidelines. In the absence of definitive histologic features, this important distinction can be challenging and time-consuming, and requires confirmatory immunohistochemical stains.

Also, a LUAD diagnosis will prompt the search for molecular biomarkers and sensitizing mutations and thus has a great impact on treatment options. For example, epidermal growth factor receptor (EGFR) mutations, present in about 20% of LUAD, and anaplastic lymphoma receptor tyrosine kinase (ALK) rearrangements, present in <5% of LUAD, currently have targeted therapies approved by the Food and Drug Administration (FDA). Mutations in other genes, such as KRAS and tumor protein P53 (TP53) are very common (about 25% and 50%, respectively) but have proven to be particularly challenging drug targets so far. Lung biopsies are typically used to diagnose lung cancer type and stage. Virtual microscopy of stained images of tissues is typically acquired at magnifications of 20× to 40×, generating very large two-dimensional images (10,000 to >100,000 pixels in each dimension) that are oftentimes challenging to visually inspect in an exhaustive manner. Furthermore, accurate interpretation can be difficult, and the distinction between LUAD and LUSC is not always clear, particularly in poorly differentiated tumors; in this case, ancillary studies are recommended for accurate classification. To assist experts, automatic analysis of lung cancer whole-slide images has been recently studied to predict survival outcomes and classification. For the latter, Yu et al. combined conventional thresholding and image processing techniques with machine-learning methods, such as random forest classifiers, support vector machines (SVM) or Naive Bayes classifiers, achieving an AUC of ~0.85 in distinguishing normal from tumor slides, and ~0.75 in distinguishing LUAD from LUSC slides. More recently, deep learning was used for the classification of breast, bladder and lung tumors, achieving an AUC of 0.83 in classification of lung tumor types on tumor slides from The Cancer Genome Atlas (TCGA). Analysis of plasma DNA values was also shown to be a good predictor of the presence of non-small cell cancer, with an AUC of ~0.94 in distinguishing LUAD from LUSC, whereas the use of immunochemical markers yields an AUC of ~0.941.

SUMMARY

In this study, a deep convolutional neural network (inception v3) was trained on whole-slide images obtained from The Cancer Genome Atlas to accurately and automatically classify them into LUAD, LUSC or normal lung tissue. The performance of our method is comparable to that of pathologists, with an average area under the curve (AUC) of 0.97. The described system and processes were validated on independent datasets of frozen tissues, formalin-fixed paraffin-embedded tissues and biopsies. Furthermore, we trained the network to predict the ten most commonly mutated genes in LUAD. We found that mutations (in the examples, STK11, EGFR, FAT1, SETBP1, KRAS and TP53) can be predicted from pathology images, with AUCs from 0.733 to 0.856 as measured on a held-out population. These findings suggest that deep-learning models can assist pathologists in the detection of cancer subtype or gene mutations.

At least one aspect of the present disclosure is directed to a method of determining cell genotype. The method includes obtaining images of a plurality of cell. The method includes analyzing the images with a machine learning device. The method includes determining predicted genotype of the plurality of cells based on the analyzed images. The method includes generating a map of spatial heterogeneity based upon the predicted genotype.

In some embodiments, the method includes classifying, by the machine learning device, the images into at least one of normal tissue or cancerous tissue based on predicted mutations identified from histopathology data. In some embodiments, the method includes classifying, by the machine learning device, the images into at least one of normal lung tissue, lung adenocarcinoma, or lung squamous cell carcinoma, based on predicted mutations identified from histopathology data. In some embodiments, the method includes classifying, by the machine learning device the images into at least one of normal tissue or cancerous tissue with an AUC of greater than 0.95. In some embodiments, the method includes distinguishing, by the machine learning device, between lung adenocarcinoma and lung squamous cell carcinoma with an AUC of greater than 0.95. In some embodiments, the method includes tiling, by the machine learning device, the images into sets of windows of between 75×75 µm to 1000×1000 µm. In some embodiments, the method includes labeling, by the machine learning device, the images using information obtained from at least one of molecular testing or staining.

In some embodiments, the method includes predicting, by the machine learning device, a mutated gene in lung adenocarcinoma, the mutated gene comprising at least one of STK11, EGFR, SETBP1, TP53, FAT1, KRAS, KEAP1, LRP1B, FAT4, or NF1.

In some embodiments, the predicted genotype is at least one of normal lung tissue, lung adenocarcinoma, or lung squamous cell carcinoma. In some embodiments, the plurality of cells are lung cells. In some embodiments, the method includes identifying a course of treatment based on the predicted genotype of the plurality of cells. In some embodiments, the method includes supplementing a pathologist's classification of whole-slide images of lung tissue.

At least one aspect of the present disclosure is directed to a computer-implemented machine for identifying tumors. The computer-implemented machine includes a processor. The computer-implemented machine includes a tangible computer-readable medium operatively connected to the processor and including computer code. The computer code is configured to receive image data regarding a region of interest. The computer code is configured to tile images into sets of windows of between 75×75 μm to 1000×1000 μm. The computer code is configured to analyze each of the windows with a machine learning system to identify phenotypic information for each of the windows. The computer code is configured to predict genotypic information for each window from the phenotypic information. The computer code is configured to generate a heatmap for the region of interest based on the predicted genotypic information for each window.

In some embodiments, the computer code is configured to classify the images into at least one of normal tissue or cancerous tissue. In some embodiments, the computer code is configured to classify the images into at least one of normal lung tissue, lung adenocarcinoma, or lung squamous cell carcinoma. In some embodiments, the computer code is configured to classify the images into at least one of normal tissue or cancerous tissue with an AUC of greater than 0.95. In some embodiments, the computer code is configured to distinguish between lung adenocarcinoma and lung squamous cell carcinoma with an AUC of greater than 0.95. In some embodiments, the computer code is configured to predict a mutated gene in lung adenocarcinoma, the mutated gene comprising at least one of STK11, EGFR, SETBP1, TP53, FAT1, KRAS, KEAP1, LRP1B, FAT4, or NF1. In some embodiments, the predicted genotypic information is at least one of normal lung tissue, lung adenocarcinoma, or lung squamous cell carcinoma. In some embodiments, the computer code is configured to identify a course of treatment based on the predicted genotypic information.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 1A shows the number of whole-slide images per class. FIG. 1B shows strategy for training. FIG. 1Bi shows images of lung cancer tissues were first downloaded from the Genomic Data Commons database; FIG. 1Bii shows slides were then separated into a training (70%), a validation (15%) and a test set (15%); FIG. 1Biii shows slides were tiled by nonoverlapping 512-×512-pixel windows, omitting those with over 50% background; FIG. 1Biv shows the Inception v3 architecture was used and partially or fully retrained using the training and validation tiles; FIG. 1Bv shows classifications were performed on tiles from an independent test set, and the results were finally aggregated per slide to extract the heatmaps and the AUC statistics. FIG. 1C shows size distribution of the images widths (gray) and heights (black). FIG. 1D shows distribution of the number of tiles per slide.

FIG. 3A shows distribution of probability of mutation in genes from slides where each mutation is present or absent (tile aggregation by averaging output probability). FIG. 3B shows ROC curves associated with the top four predictions in a. FIG. 3C shows Allele frequency as a function of slides classified by the deep-learning network as having a certain gene mutation (P≥0.5) or the wild type (P<0.5). P values were estimated with the two-tailed Mann-Whitney U-test and are shown as nonsignificant (n.s.; P>0.05). *P≤0.05, P≤0.01 or *P≤0.001. For a, b and c, 62 slides from 59 patients. For the two box plots, whiskers represent the minima and maxima. The middle line within the box represents the median.

FIG. 4A shows probability distribution on LUAD tiles for the six predictable mutations, with average values in dotted lines (n=327 nonoverlapping tiles). The allele frequency is 0.33 for TP53, 0.25 for STK11, and 0 for the four other mutations. FIGS. 4B-E show heatmaps of TP53 (FIGS. 4B, 4D) and STK11 (FIGS. 4C, 4E) when only tiles classified as LUAD are selected (FIGS. 4B, 4C), and when all the tiles are considered (FIGS. 4D, 4E). Scale bars, 1 mm.

FIG. 6A shows per-slide Receiver Operating Characteristic (ROC) curves after classification of normal versus tumor images (using 20× magnified tiles)

resulted in an almost error-free classification. FIG. 6B shows the ROC curves obtained after transfer learning for LUAD vs LUSC images classification show inferior performance compared to those obtained from FIG. 6C fully trained network. Aggregation was either done by averaging the probability scores (purple ROC curves) or by counting the percentage of properly classified tiles (green ROC curves). In all panels, the crosses correspond to the manual classification of LUAD vs LUSC slides by pathologists. FIG. 6D shows multi-class ROC of the Normal vs LUAD vs LUSC classification yields the best result for overall classification of cancer types. Dotted lines are negative control trained and tested after random label assignments. In FIGS. 6E and 6F, training and testing in FIGS. 6C and 6D were replicated using tiles at 5× magnification instead of 20×. The ROC curves show that performance is similar for both magnifications. n=244 slides for FIGS. 6B, 6C, and 6E, and n=170 slides for FIGS. 6A, 6D, and 6F, all from 137 patients. FIG. 6G shows comparison of AUCs obtained with different techniques for classification of normal and (FIG. 6H) of cancer type slides (For Terry et al., stands for Immunoschemistry. For Khosravi et al., data from inter-images tests on the TCGA and Stanford Tissue Microarray databases are displayed). FIG. 6I shows proportion of LUAD and LUSC slides misclassified by the pathologists as a function of the true positive probability assigned in FIG. 6C. The number of slides are indicated on the bars.

FIG. 7A shows tumor content distributions and AUCs across datasets after manual tumor selection, no selection and automatic selection using a deep learning model (for Frozen, FFPE and Biopsies respectively, n=98, 140 and 102 biologically independent slides; whiskers represent the minima and maxima. The middle line within the box represents the median; the AUC values are shown with the error bars representing the 95% CIs), FIG. 7B shows the difference in AUC compared to manual tumor selection (20× magnification).

FIG. 9A shows mutation probability distribution for slides where each mutation is present and absent after tile aggregation done by counting the percentage of tiles properly classified. n=62 slides from 59 patients. p-values estimated with two-tailed Mann-Whitney U-test are shown as ns ($p>0.05$), *($p\leq0.05$), ($p\leq0.01$) or * ($p\leq0.001$). Whiskers represent the minima and maxima. The middle line within the box represents the median. FIG. 9B shows ROC curves associated with FIG. 9A.

FIG. 10A shows scatterplots where each point represents a tile where the color is proportional to the mutation probability generated by the deep learning network. FIG. 10B shows tile-embedded t-SNE representation with zooms on clusters having specific mutation predictions. n=24,144 tiles of 62 slides from 59 patients.

FIGS. 13A and 13B show typical examples of LUAD and LUSC whole-slide images. FIGS. 13C and 13D show the corresponding heatmaps with probabilities of the winning class assigned to each tile such as: red for tiles classified as LUAD, blue for LUSC and grey for Normal. Training was done once.

FIG. 14A shows scatterplots where each point represents a the where the color is proportional to the probability generated by the deep learning network for each class. FIG. 14B shows tile-embedded t-SNE representation with insets showing a random selection of tiles for different regions. n=149,790 tiles of 244 slides from 137 patients.

Figure 1A:
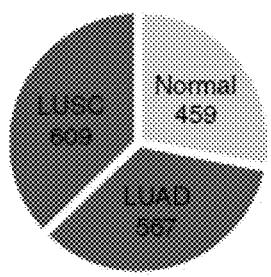
FIGS. 1A-D show data and strategy.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to classification and mutation prediction from histopathology images using deep learning. In particular, the examples described herein utilize lung cancer as an example, in particular adenocarcinoma (LUND) and squamous cell carcinoma (LUSC) as two subtypes of lung cancer to identify and distinguish between.

Described herein are systems and methods utilizing deep learning on convolutional neural networks (CNNs) that not only outperforms methods in previously published work, but also achieves accuracies that are comparable to pathologists while providing benefits of a non-human method of identification. Most importantly, the methods described herein maintain their performance when tested on independent datasets of both frozen and formalin-fixed paraffin-embedded (FFPE) tissues as well as on images obtained from biopsies.

CNNs have also been studied with regard to classification of lung patterns on computerized tomography (CT) scans, achieving an f-score of ~85.5%. To study the automatic classification of lung cancer whole-slide images, we used the inception v3 architecture and whole-slide images of hematoxylin and eosin (H&E)-stained lung tissue from TCGA obtained by surgical excision followed by frozen section preparation. In 2014, Google won the ImageNet Large-Scale Visual Recognition Challenge by developing the GoogleNet architecture, which increased the robustness to translation and nonlinear learning abilities by using microarchitecture units called inception. Each inception unit includes several nonlinear convolution modules at various resolutions. Inception architecture is particularly use for processing the data in multiple resolutions, a feature that makes this architecture suitable for pathology tasks. This network has already been successfully adapted to other specific types of classifications like skin cancers and diabetic retinopathy detection.

While the process and systems herein describe generally the identification of mutations, it should be appreciated that in general the process and systems can be utilized to identify a phenotype from the image data and the like to identify a genotype, gene mutations, molecular groups/families or mutational burden.

In a particular embodiment, the methods and system further provide for the generation of a map of tumor spatial heterogeneity. The map is generated based upon predicted mutations identified from the histopathology data processed by the machine learning device. Tumor heterogeneity describes the observation that different tumor cells can show distinct morphological and phenotypic profiles, including cellular morphology, gene expression, metabolism, motility, proliferation, and metastatic potential. This phenomenon occurs both between tumors (inter-tumor heterogeneity) and within tumors (intra-tumor heterogeneity). Thus, the process described herein can further include the identification of a genotype (such as a particular known mutation) of cells or a defined segment of cells in an observed phenotype of the tumor.

In a further embodiment, the identification of particular mutations can be assessed for the entirety of an identified tumor or for a particular region of interest. That can be expressed in terms of the percentage of cells in that tumor or region of interest that have defined genotypes, such as x % of a particular mutation.

In a further embodiment, a course of treatment can be identified based on one or more of the identified phenotype of a cell or the collective identified phenotype of a tumor or region of interest, the predicted genotype of a cell or the collective predicted genotype of a tumor or region of interest, or the predicted heterogeneity of a tumor or region of interest.

While specific processes are described further below in the examples, one particular embodiment includes the following steps for the localization of gene mutations, molecular groups/families or mutational burden. First, slides need to be tiled into small relevant windows. In one embodiment, windows of 75×75 um to 1000×1000 um, preferably 500× 500 or 250×250 but can be larger, or as small as a cell depending on the application. Second, slides and tiles are labelled using information Obtained from molecular testing, staining, or similar accepted techniques. Third, optionally but preferably, the image is segment into regions to pre-identify where the mutated cells are most likely occurring (tumor regions for example) using either manual selection from an expert, a CNN-trained network or an auto-encoder. Fourth, the network is trained using raw tiles pre-selected by the previous segmentation step. It should be appreciated that once the training has been done, this step may be skipped and a trained system may be used directly. Further, the machine learning system may include a learning algorithm to provide further feedback even once trained. In one embodiment, to increase the performance, instead of the original 3-channel color image, a training job on a data-enlarged image (including more than just the 3-channel color image) is included. Those channels contain additional information, for example but not limited to: adjacent tiles, current tile pre-segmented with conventional image processing tools to highlight cells or regions of interest, non-linear image transformations, coded data from the patient [age, sex and other medically relevant information], etc.). Fifth, for sets of images that are run through the trained system, generate a heatmap using the output of the previously trained system.

Experiments

A deep-learning framework for the automatic analysis of histopathology images. A study was undertaken as an experiment to test exemplary systems and methods described above. As noted above, lung cancer, specifically LUSC and LUAD subtypes were chosen for further study and proof of concept. The experimental setup and outcome are described below and the relation of the experimental results to the general methods and systems is discussed further below in the Experimental Results section.

Figure 1B:
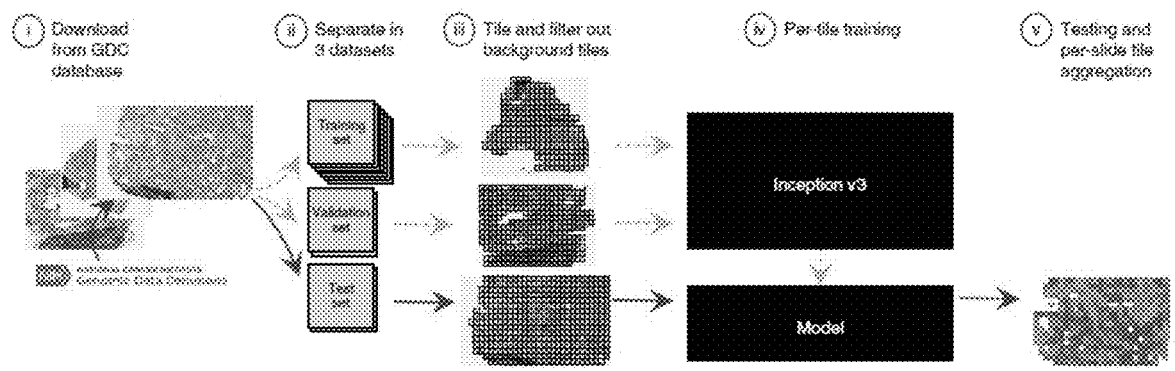
Figure 1C:
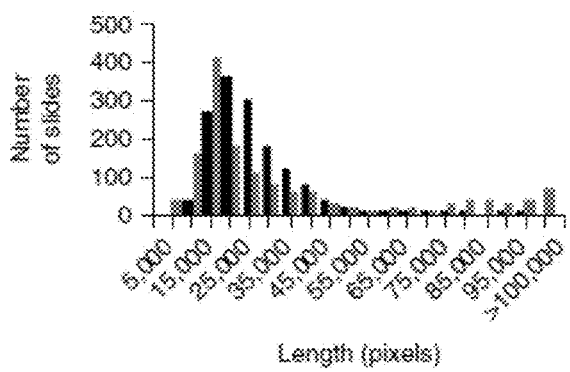
Figure 1D:
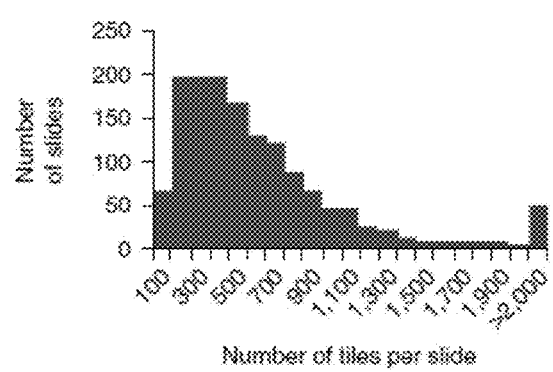

With regard to the experiments, TCGA dataset characteristics and the overall computational strategy are summarized in FIGS. 1A-D (Methods). We used 1,634 whole-slide images from the Genomic Data Commons database: 1,176 tumor tissues and 459 normal tissues (FIG. 1A). The 1,634 whole-slide images were split into three sets: training, validation and testing (FIG. 1B). Importantly, this ensures that our model is never trained and tested on tiles (see below) obtained from the same tumor sample. Because the sizes of the whole-slide images are too large to be used as direct input to a neural network (FIG. 1C), the network was instead trained, validated and tested using 512×512 pixel tiles, obtained from non-overlapping 'patches' of the whole-slide images. This resulted in tens to thousands of tiles per slide, depending on the original size (FIG. 1D).

Figure 5:
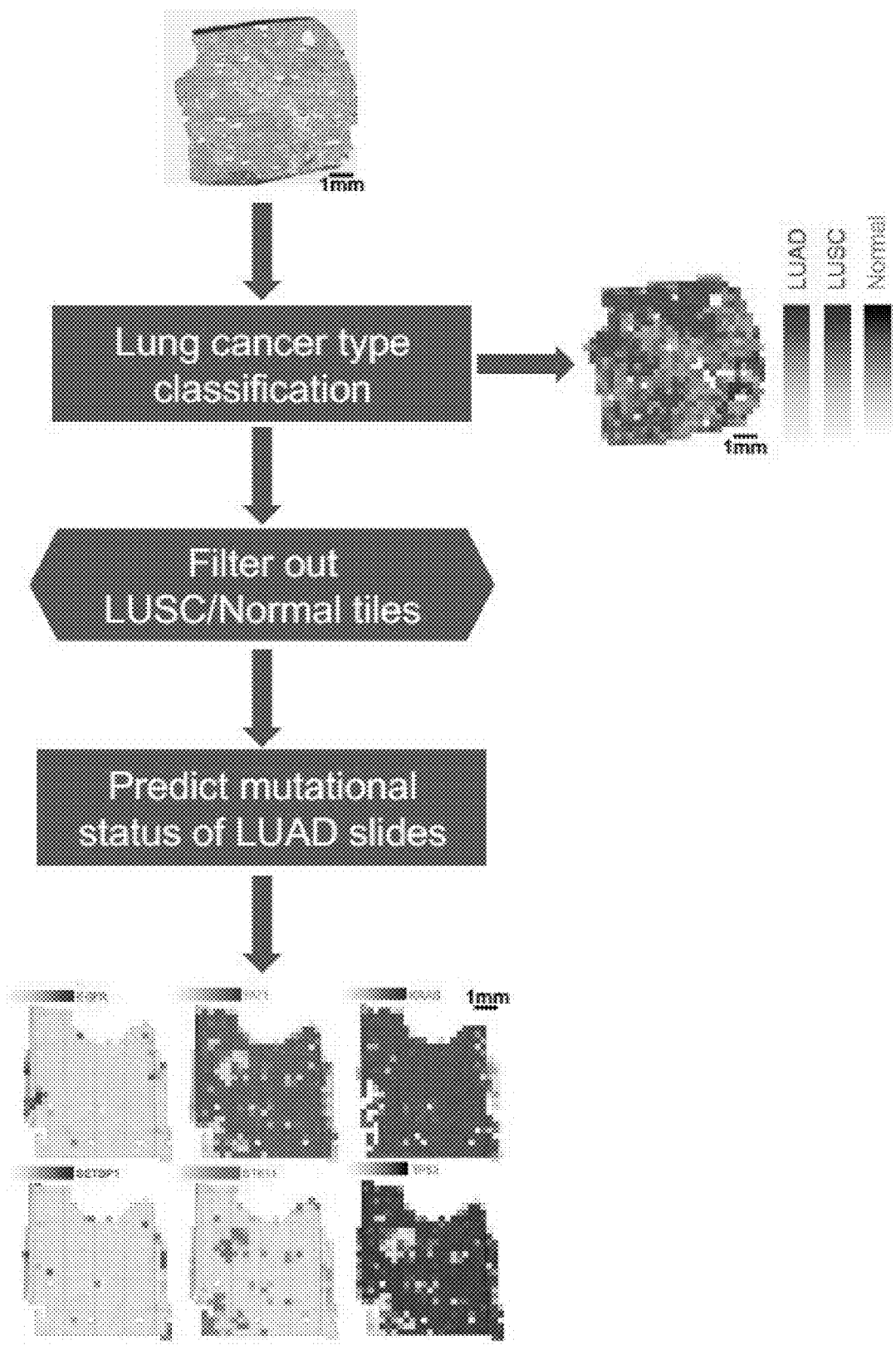
FIG. 5 shows workflow of the computational analysis of H&E scans of lung tissues. The images are first run through a first classifier to determine the lung cancer types and identify the regions where LUAD cancer is present. Then, the mutation prediction network is run on those regions.

Based on the computational strategy outlined in FIG. 1B, we present two main results. First, we develop classification models that classify whole-slide images into normal lung, LUAD or LUSC with an accuracy that is significantly higher than previous work (AUC of 0.97 compared to 0.75 and 0.83) and comparable to results from pathologists. Unlike previous work, the performance of our classification models was tested on several independent datasets: biopsies and surgical resection specimens either prepared as frozen sections or as FFPE tissue sections. Second, starting with the LUAD regions as predicted by the LUAD versus LUSC versus normal classification model, we utilize the same computational pipeline (FIG. 1B) to train a new model in order to predict the mutational status of frequently mutated genes in lung adenocarcinoma using whole-slide images as the only input. The entire workflow of our computational analysis is summarized in FIG. 5.

Figure 6A:
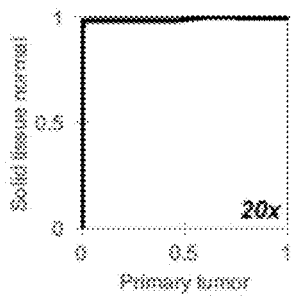
FIGS. 6A-I show accurate Classification of lung cancer histopathology images.

Deep-learning models generate accurate diagnosis of lung histopathology images. Using the computational pipeline of FIG. 1B, we first trained inception v3 to recognize tumor versus normal. To assess the accuracy on the test set, the per-tile classification results were aggregated on a per-slide basis either by averaging the probabilities obtained on each tile or by counting the percentage of tiles positively classified, thus generating a per-slide classification (Methods). The former approach yielded an AUC of 0.990, and the latter yielded 0.993 (FIG. 6A and Table 1) for normal-versus-tumor classification, outperforming the AUC of ~0.85 achieved by the feature-based approach of Yu et al., of ~0.94 achieved by plasma DNA analysis and comparable or better than molecular profiling data (Table 2).

TABLE 1

Area Under the Curve (AUC) achieved by the different classifiers (with 95% CIs) (n = 244 slides for LUAD vs LUSC classifiers and n = 170 slides for the others, all from 137 patients).

| | | AUC after aggregation by . . . | |
|---|---|---|---|
| Classification | Information | . . . average predicted probability | . . . percentage of positively classified tiles |
| Normal vs Tumor (20x tiles) | a) Inception v3, fully-trained | 0.993 [0.974-1.000] | 0.990 [0.969-1.000] |
| LUAD vs LUSC (20x tiles) | b) Inception v3, transfer learning | 0.847 [0.782-0.906] | 0.844 [0.777-0.904] |
| | c) Inception v3, fully-trained | 0.950 [0.913-0.980] | 0.947 [0.911-0.978] |
| | d) Same as (c) but aggregation done solely on tiles classified as "tumor" by A | 0.952 [0.915-0.981] | 0.949 [0.912-0.980] |
| LUAD vs LUSC (5x tiles) | Inception v3, fully-trained | 0.942 [0.907-0.971] | 0.906 [0.851-0.951] |
| 3 classes. Normal vs LUAD vs LUSC at 20x | Normal | 0.984 [0.947-1.000] | 0.985 [0.953-1.000] |
| | LUAD | 0.969 [0.933-0.994] | 0.970 [0.937-0.993] |
| | LUSC | 0.966 [0.935-0.990] | 0.964 [0.932-0.989] |
| | Micro-average | 0.970 [0.950-0.986] | 0.969 [0.949-0.985] |
| | Macro-average | 0.976 [0.949-0.993] | 0.976 [0.950-0.993] |
| 3 classes. Normal vs LUAD vs LUSC at 5x | Normal | 0.997 [0.993-0.998] | 0.988 [0.962-1.000] |
| | LUAD | 0.965 [0.942-0.983] | 0.938 [0.896-0.971] |
| | LUSC | 0.977 [0.960-0.991] | 0.964 [0.937-0.986] |
| | Micro-average | 0.980 [0.972-0.987] | 0.966 [0.948-0.980] |
| | Macro-average | 0.981 [0.968-0.991] | 0.964 [0.939-0.980] |

TABLE 2

Diagnostic performance based on molecular profiling data.

| Author | Method | Normal vs NSCLC | LUAD vs LUSC | Cohort size | Test on independent cohorts |
|---|---|---|---|---|---|
| Girard | 62-gene microarray panel | Accuracy = 86% Sensitivity = 83% Specificity = 100% | Accuracy = 93% Sensitivity = 95% Specificity = 89% | 1337 lung cancer; 191 healthy controls | Yes |
| Charkiewicz | 53-gene microarray panel | | Accuracy = 92.7% Sensitivity = 100% Specificity = 88% | 152 LUSC and LUAD tissue | Yes |
| Hou | 5-gene microarray | Accuracy = 97% | Accuracy = 84% | 91 NSCLC; 65 adjacent | Yes |

TABLE 2-continued

Diagnostic performance based on molecular profiling data.

| Author | Method | Normal vs NSCLC | LUAD vs LUSC | Cohort size | Test on independent cohorts |
|---|---|---|---|---|---|
| Wilkerson | 57-gene microarray panel | | Accuracy = 78% (additional categories) | normal lung tissue 442 lung cancer with adjacent normal lung tissue | Yes |
| Bhattacharjee | 52-gene microarray panel | Accuracy = 85% (81%-89%) | Accuracy = 85% (additional categories) | 186 lung cancer, 17 normal lung tissue | No |
| Cuezva | protein expression of a 3-gene panel from tissue samples | Accuracy = 91.4% Sensitivity = 97.3% (LUAD vs normal) | | 90 LUAD, 10 normal lung tissue | No |
| Amachika | RT-qPCR for NOK mRNA in peripheral blood | Sensitivity = 80.5% Specificity = 92.3% | | 41 lung cancer; 13 healthy controls | No |
| Du | RT-qPCR for STC1 mRNA levels in peripheral blood | AUC = 0.969 | | 65 lung cancer; 52 healthy controls | No |
| Cheng | RT-qPCR for LunX mRNA levels in peripheral blood | Sensitivity = 92.9% Specificity = 75.0% | | 44 lung cancer; 15 healthy controls | No |
| Sheu | RT-qPCR for 3-gene mRNA panel in peripheral blood | AUC = 0.887 | | 69 lung cancer; 100 healthy controls | No |

Figure 6B:
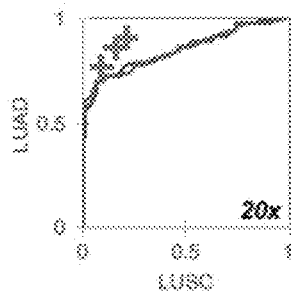
Figure 6C:
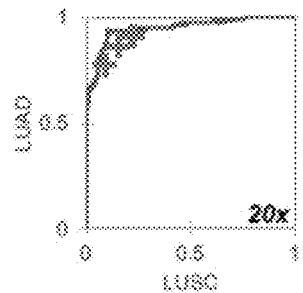

Next, we tested the performance of our approach on the more challenging task of distinguishing, LUAD and LUSC. To do this, we first tested whether convolutional neural networks can outperform the published feature-based approach, even when plain transfer learning is used. For this purpose, the values of the last layer of inception v3 previously trained on the ImageNet dataset to identify 1,000 different classes were initialized randomly and then trained for our classification task. After aggregating the statistics on a per-slide basis (FIG. 6B), this process resulted in an AUC of 0.847 (Table 11) i.e., a gain of ~0.1 in AUC compared to the best results obtained by Yu et al. using image features combined with random forest classifier. The performance can be further improved by fully training inception v3, leading to an AUC of 0.950 when the aggregation is done by averaging the percentile probabilities (FIG. 6C). These AUC values are improved by another 0.002 when the tiles previously classified as 'normal' by the first classifier are not included in the aggregation process (Table 1).

Figure 6D:
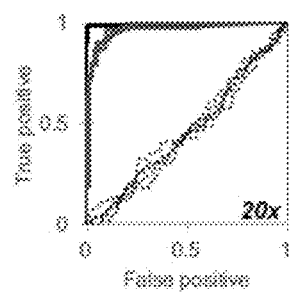
Figure 6E:
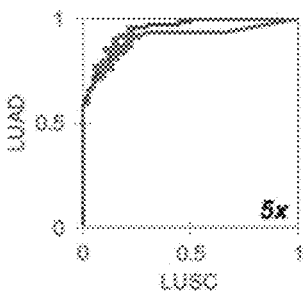
Figure 6F:
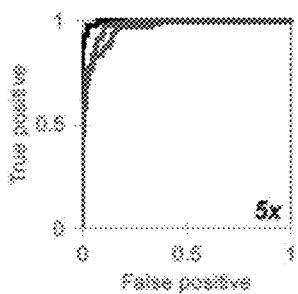
Figure 6G:
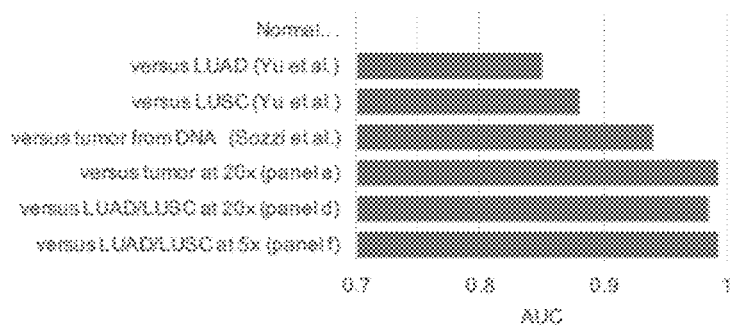
Figure 6H:
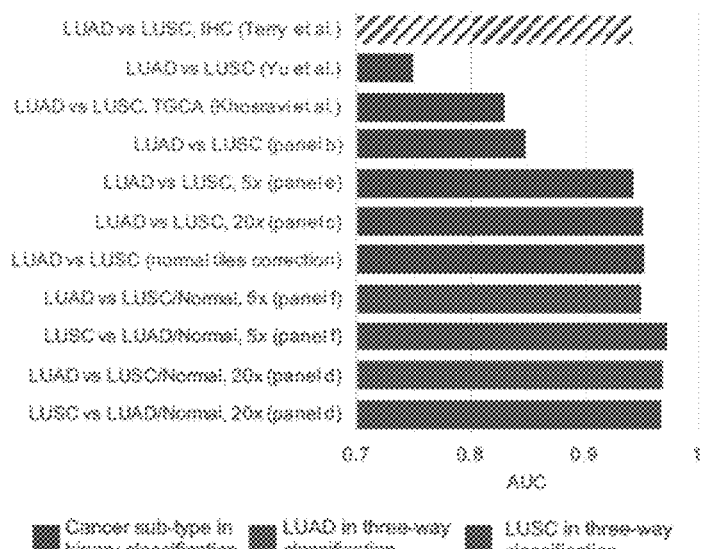

We further evaluated the performance of the deep-learning model by training and testing the network on a direct three-way classification into the three types of images (normal, LUAD, LUSC). Such an approach resulted in the highest performance with all the AUCs improved to at least 0.968 (FIG. 6D and Table 1). In addition to working with tiles at 20× magnification, we investigated the impact of the magnification and field of view of the tiles on the performance of our models. As low-resolution features (nests of cells, circular patterns) may also be useful for classification of lung cancer type, we used slides showing a larger field of view to train the model by creating 512-×512-pixel tiles of images at 5× magnification. The binary and three-way networks trained on such slides led to similar results (FIGS. 6E-F and Table 1). FIGS. 6G-H and Table 2 summarize and compare the performance of the different approaches explored in this study and in previous work.

Figure 6I:
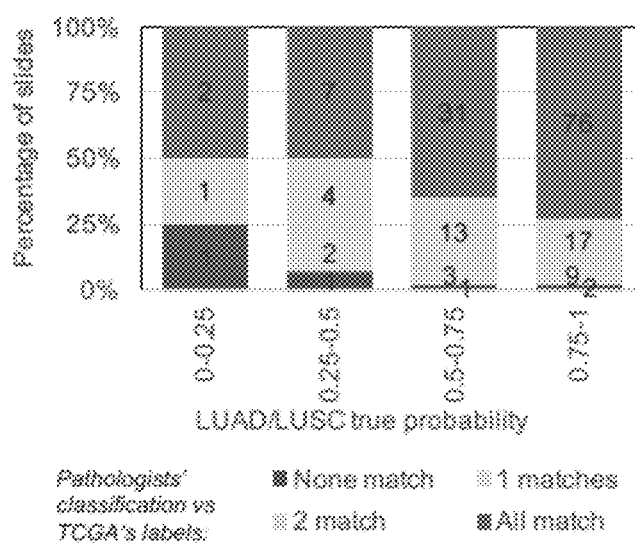

Comparison of deep-learning model to pathologists. We then asked three pathologists (two thoracic pathologists and one anatomic pathologist) to independently classify the whole-slide H&E images in the test set by visual inspection alone, independently of the classification provided by TCGA. Overall, the performance of our models was comparable to that of each pathologist (FIGS. 6B-F, pink cross). FIG. 6I shows that 152 slides in our test set have a true positive probability above 0.5 (according to our model), and for 18 slides, this probability is below 0.5. Of the slides that were incorrectly classified by our model, 50% were also misclassified by at least one of the pathologists, whereas 83% of those incorrectly classified by at least one of the pathologists (45 out of 54) were correctly classified by the algorithm. We then measured the agreement between the TCGA classification and that of each pathologist, of their consensus and finally of our deep-learning model (with an optimal threshold leading to sensitivity and specificity of 89% and 93%) using Cohen's Kappa statistic (Table 3). We observed that the agreement of the deep-learning model with TCGA was slightly higher (0.82 versus 0.67 for pathologist 1, 0.70 for pathologist 2, 0.70 for pathologist 3, and 0.78 for the consensus) but did not reach statistical significance (P values of 0.035, 0.091, 0.090 and 0.549, respectively, estimated by a two-sample two-tailed z-test score). Regarding time effort, it can take a pathologist one to several minutes to analyze a slide depending on the difficulty of distinguishing each case.

TABLE 3

Inter-pathologists and binary deep-learning method variability estimated with the Cohen's Kappa statistic (n = 170 slides from 137 patients; * thoracic pathologists; ** anatomic pathologist)

|  | Pathologist 1* | Pathologist 2** | Pathologist 3* | Consensus between pathologists | Deep-learning |
|---|---|---|---|---|---|
| TCGA | 0.67 | 0.70 | 0.70 | 0.78 | 0.82 |
|  | CIs = [.56-8.78] | CIs = [.60-.81] | CIs = [.59-.81] | CIs = [.69-.88] | CIs = [.74-.91] |
| Pathologist 1 |  | 0.52 | 0.55 | 0.56 | 0.64 |
|  |  | CIs = [.39-.65] | CIs = [.42-.67] | CIs = [.44-.69] | CIs = [.52-.75] |
| Pathologist 2 |  |  | 0.78 | 0.65 | 0.63 |
|  |  |  | CIs = [.69-.88] | CIs = [.54-.77] | CIs = [.52-.75] |
| Pathologist 3 |  |  |  | 0.75 | 0.60 |
|  |  |  |  | CIs = [65-.86] | CIs = [.48-.72] |
| Consensus between pathologists |  |  |  |  | 0.77 |
|  |  |  |  |  | CIs = [.68-.87] |

Furthermore, in the absence of definitive histologic features, confirmatory immunohistochemical stains are required and can delay diagnosis for up to 24 h. The processing time of a slide by our algorithm depends on its size; currently, it takes ~20 s to calculate per-tile classification probabilities on 500 tiles (the median number of tiles per slide is <500) on a single Tesla K20 m GPU. Considering the possibility of using multiple GPUs to process tiles in parallel, classification using our model can be executed in a few seconds. The scanning time of each slide using the Aperio scanner (Leica) is currently 2-2.5 min for a slide at 20×, but with the 2017 FDA approval of the new ultra-fast digital pathology scanner from Philipps, this step will probably no longer be bottleneck in the near future.

Figure 2A:
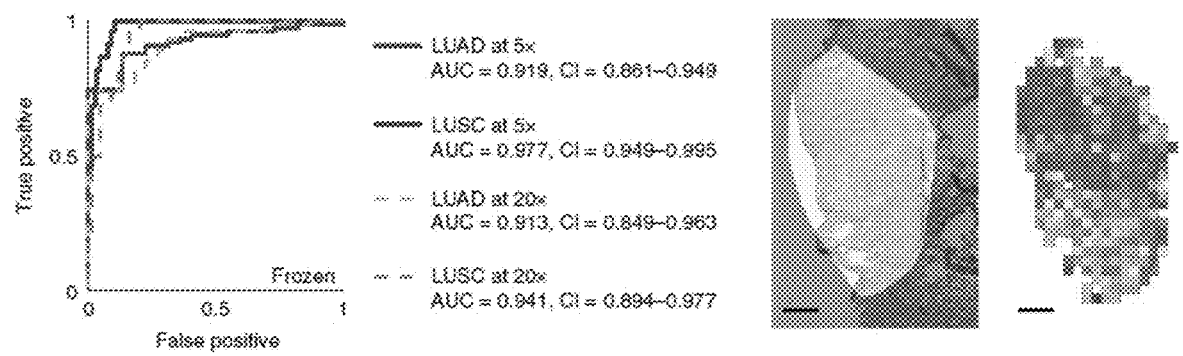
FIGS. 2A-C show classification of presence and type of tumor on alternative cohorts: receiver operating characteristic (ROC) curves (left) from tests on frozen sections (n=98 biologically independent slides) (FIG. 2A), FFPE sections (n=140 biologically independent slides) (FIG. 2B) and biopsies (n=102 biologically independent slides) from NYU Langone Medical Center (FIG. 2C). On the right of each plot, we show examples of raw images with an overlap in light gray of the mask generated by a pathologist and the corresponding heatmaps obtained with the three-way classifier. Scale bars, 1 mm.
Figure 2B:
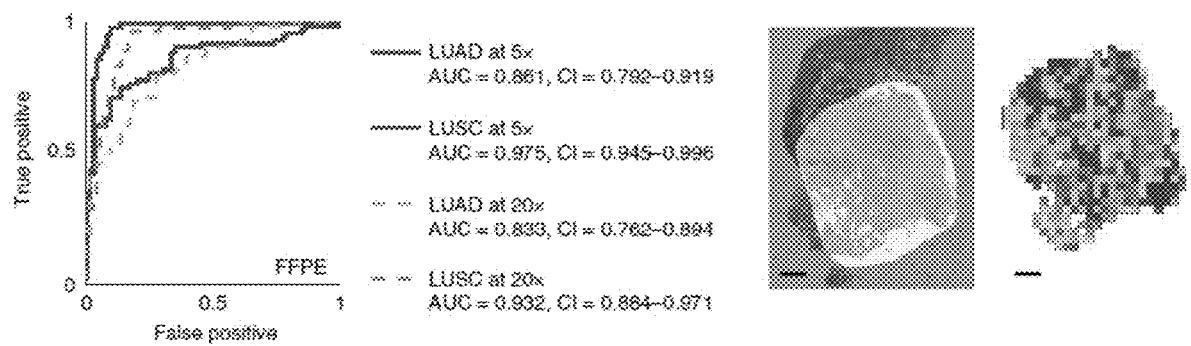
Figure 2C:
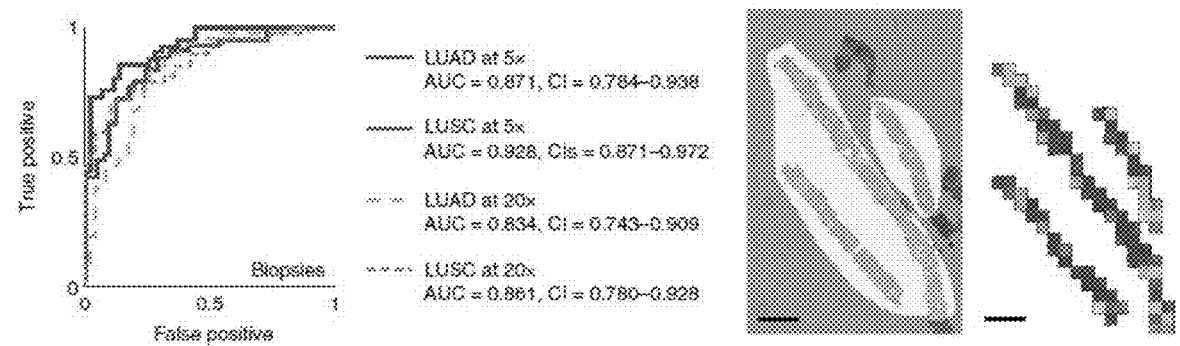

Testing on independent cohorts demonstrates generalizability of the neural network model. The model was then evaluated on independent datasets of lung cancer whole-slide images taken from frozen sections (98 slides) and FFPE sections (140 slides) as well as lung biopsies (102 slides) obtained at the New York University (NYU) Langone Medical Center (FIGS. 2A-C). In this case, the pathologists' diagnosis, based on morphology and supplemented by immunohistochemical stains (TTF-1 and p40 for LUAD and LUSC respectively) when necessary, was used as the gold standard (i.e., used as a ground truth to assess the performance of our approach). Each TCGA image is almost exclusively composed of either LUAD cells, LUSC cells, or normal lung tissue. As a result, several images in the two new datasets contain features that the network has not been trained to recognize, making the classification task more challenging. We observed that features, including blood clot, blood vessels, inflammation, necrotic regions, and regions of collapsed lung are sometimes labeled as bronchial cartilage is sometimes labeled as LUSC, and fibrotic scars can be misclassified as normal or LUAD.

Figure 7A:
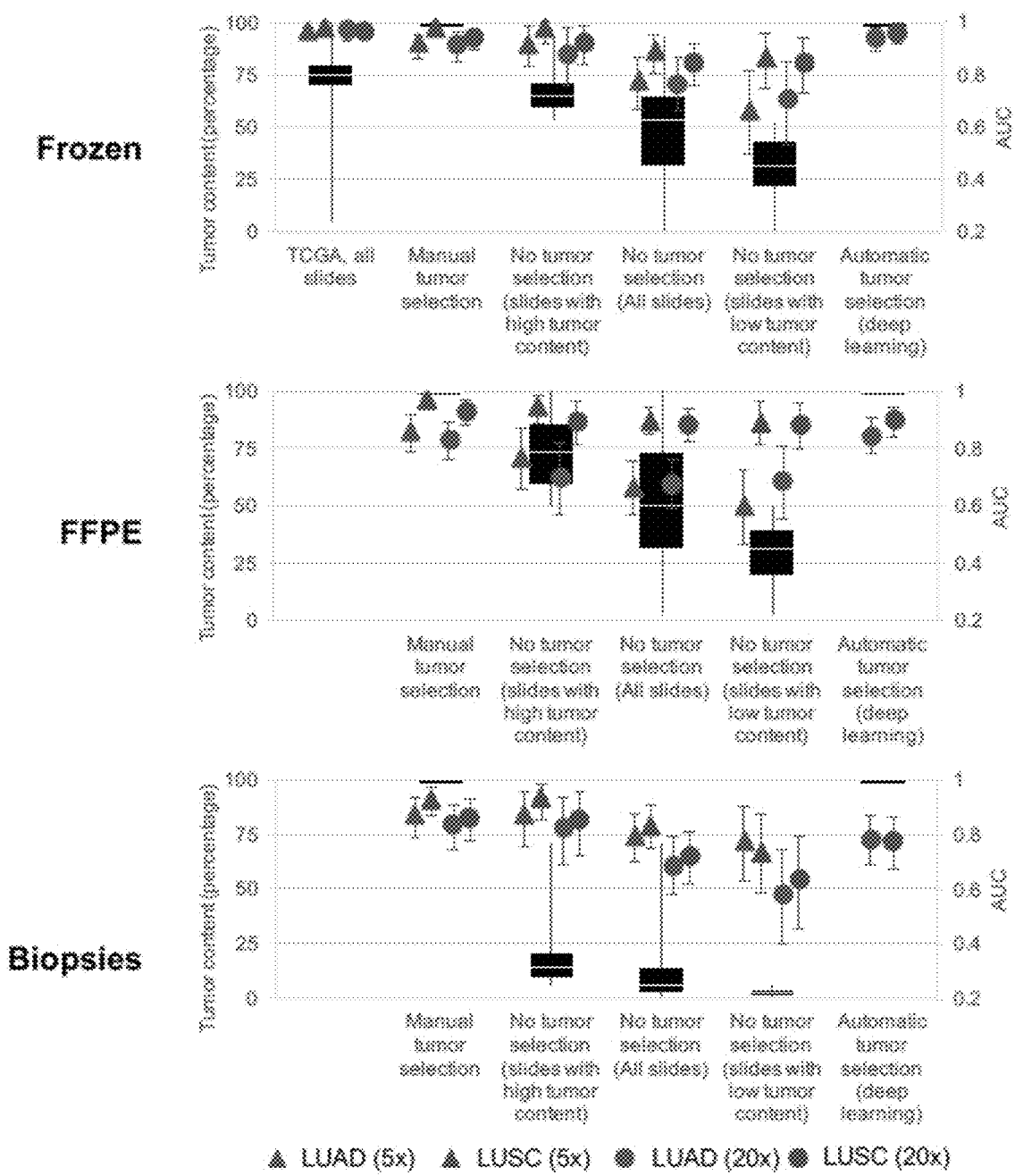
FIGS. 7A-B show the impact of tumor selection on model performance.

As demonstrated in FIG. 7A, TCGA images have significantly higher tumor content compared to the independent datasets, and tumor content correlates with the ability of the algorithm to generalize on these new unseen samples. To reduce the bias generated by some of these particular features that are found outside the tumor areas and only test the ability of our network to dissociate LUAD, LUSC and normal tissues regions, the AUCs in FIGS. 2A-C were computed on regions of high tumor content that were manually selected by a pathologist. Considering that new types of artifacts were also observed on some older slides (dull staining, uneven staining, air bubbles under the slide cover leading to possible distortion), the results obtained on these independent cohorts are very encouraging. At 20× magnification, more tiles are fully covered by some of these 'unknown' features, whereas at 5× magnification, the field of view is larger and contains features known by the classified (tumor or normal cells) in many more tiles, allowing a more accurate per-tile classification. This, in turn, leads to a more accurate per-slide classification.

Figure 8:
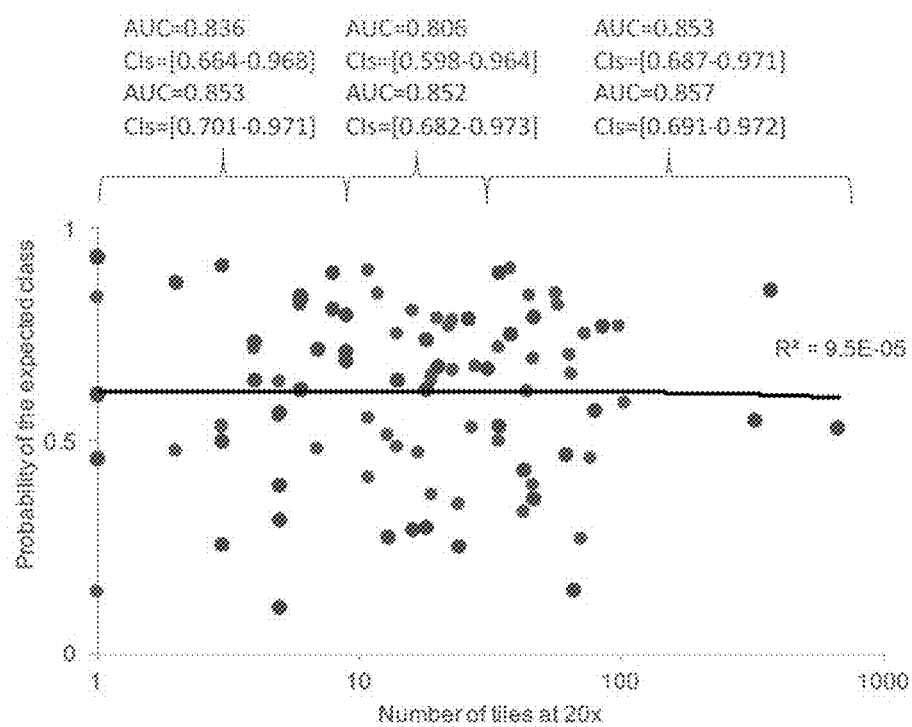
FIG. 8 shows the relationship between the number of tiles in biopsy slides versus the accuracy of the three-way classifier. R-squared is shown for the linear fit obtained by linear regression (black line) of the LUAD (red) and LUSC (blue) data points (n=102 biologically independent slides). Also, the dataset was split in 3 equal sets (same number of tiles) and AUCs were computed for slides with a low, medium or high number of tiles. AUCs are shown above the graphs.

Taken together, these observations may explain why the AUC of the classifier on 5×-magnified tiles is mostly higher than the one from 20×-magnified tiles. Interestingly, even though the slides from FFPE and biopsy sections were preserved using a different technique from those in the TCGA database, the performance remains satisfactory (FIG. 2B). For the biopsies, we noticed that poor performance was not only associated with regions where fibrosis, inflammation or blood was also present, but also in very poorly differentiated tumors. Sections obtained from biopsies are usually much smaller, which reduces the number of tiles per slide, but the performance of our model remains consistent for the 102 samples tested (AUC ~0.834-0.861 using 20× magnification and 0.871-0.928 using 5× magnification; FIG. 2C), and the accuracy of the classification does not correlate with the sample size or the size of the area selected by our pathologist (FIG. 8; $r^2=9.5\times10^{-5}$). In one-third of the cases collected, the original diagnosing pathologist was not able to visually determine the tumor type; TTF-1 and p40 stains were therefore used to identify LUAD and LUSC cases, respectively. Notably, when splitting the dataset we noticed that our model is able to classify those difficult cases as well: at 20×, the LUAD and AUCs for those difficult cases were 0.809 (confidence interval (CI), 0.639-0.940) and 0.822 (CI, 0.658-0.950, respectively, which is only slightly lower than the slides considered obvious for the pathologists (for LUAD, AUC of 0.869 (CI, 0.753-0.961) and for LUSC, 0.883 (CI, 0.777-0.962)).

Figure 7B:
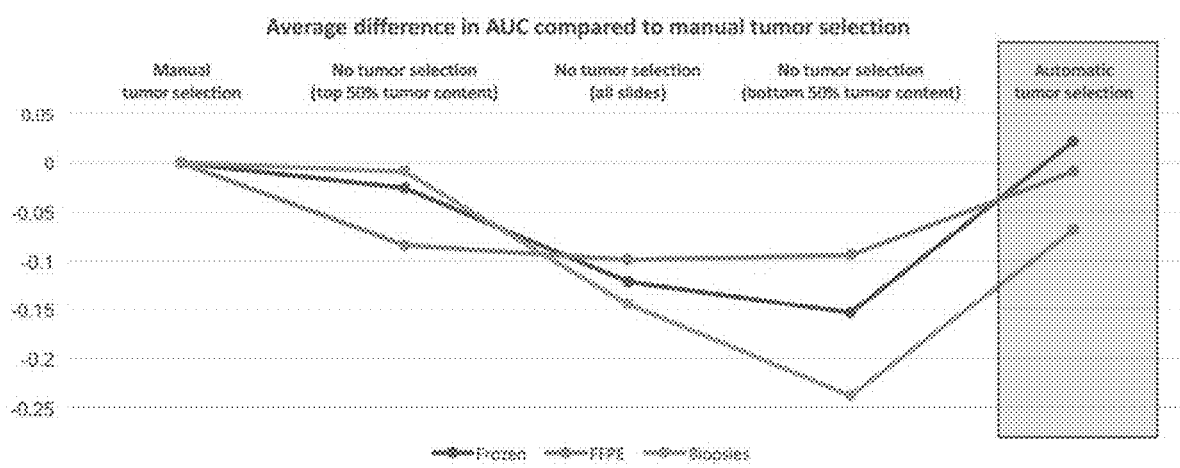

Finally, we tested whether it is possible to replace the manual tumor selection process by an automatic computational selection. To this end, we trained inception v3 to recognize tumor areas using the pathologist's manual selections. Training and validation were done on two out of the three datasets, and testing was performed on the third one. For example, to test the performance of the tumor selection model on the biopsies, we trained the model to recognize the tumor area on the frozen and FFPE samples, then applied this model to the biopsies and finally applied the TCGA-trained three-way classifier on the tumor area selected by the automatic tumor selection model. The per-tile AUC of the automatic tumor selection model (using the pathologist's tumor selection as reference) was 0.886 (CI, 0.880-0.891) for the biopsies, 0.797 (CI, 0.795-0.800) for the frozen samples, and 0.852 (CI, 0.808-0.895) for the FFPE samples. As demonstrated in FIG. 7A (right-most bar of each graph), we observed that the automatic selection resulted in a performance that was comparable to the manual selection (slightly better AUC in frozen, no difference in FFPE and slightly worse in biopsies; see also FIG. 7B).

Figure 3A:
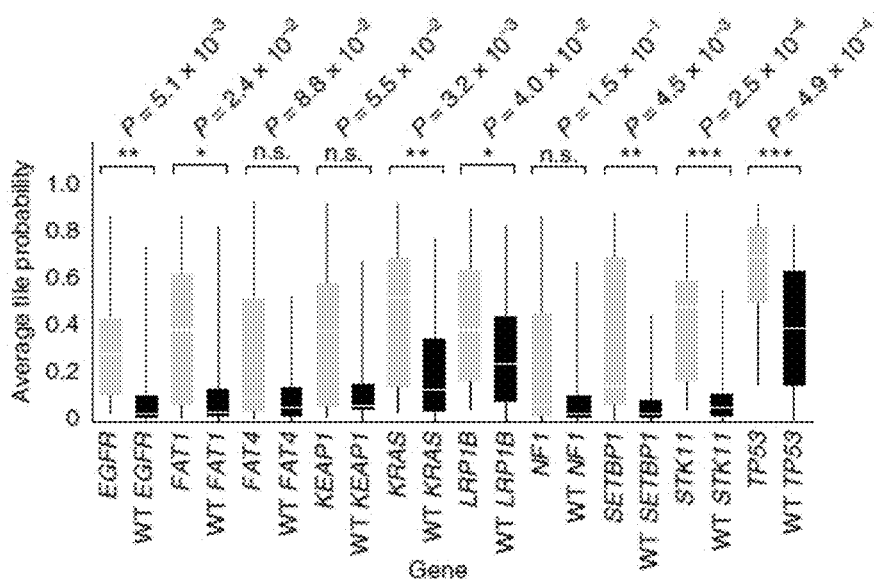
FIGS. 3A-C show gene mutation prediction from histopathology slides give promising results for at least six genes.
Figure 3B:
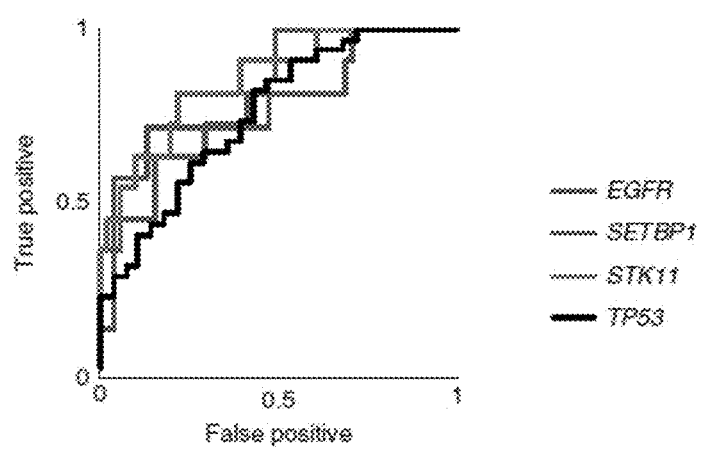
Figure 9A:
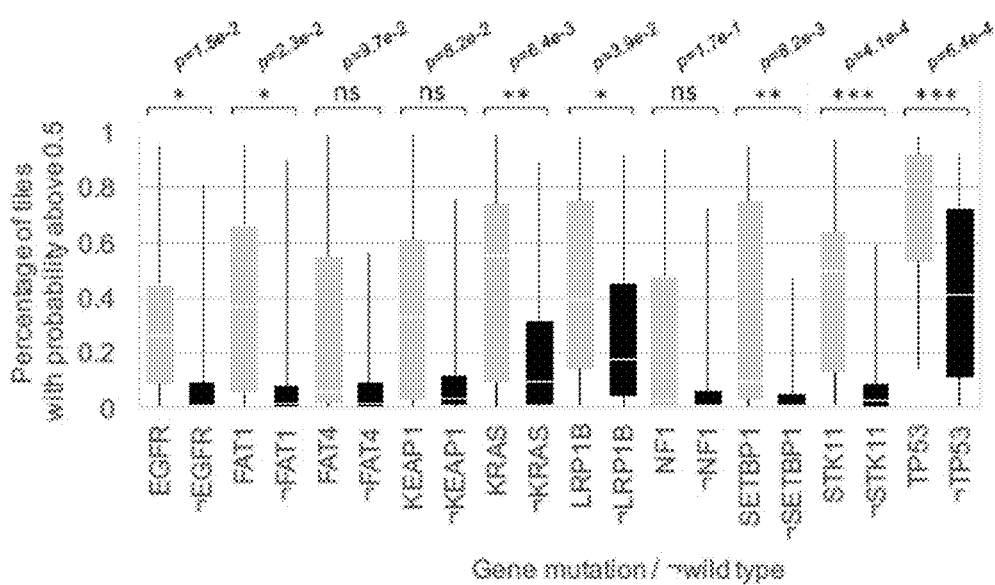
FIGS. 9A-B show gene mutation prediction from histopathology slides and the promising results for at least 6 genes.
Figure 9B:
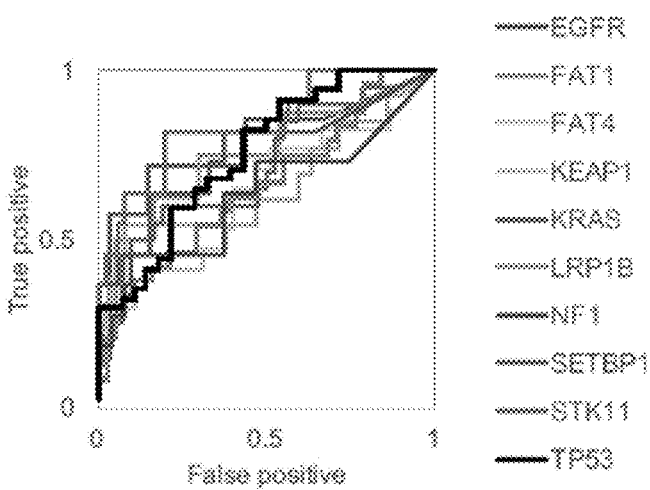

Predicting gene mutational status, from whole-slide images. We next focused on the LUAD slides and tested whether CNNs can be trained to predict gene mutations using images as the only input. For this purpose, gene mutation data for matched patient samples were downloaded from TCGA. To make sure the training and test sets contained enough images from the mutated genes, we only selected those which were mutated in at least 10% of the available tumors. From each LUAD slide, only tiles classified as LUAD by our classification model were used for this task in order to avoid biasing the network to learn LUAD-specific versus LUSC-specific mutations and to focus instead on distinguishing mutations relying exclusively on LUAD tiles. Inception v3 was modified to allow multi output classification (Methods): training and validation was conducted on ~212,000 tiles from ~320 slides, and testing was performed on ~44,000 tiles from 62 slides. Box plot and ROC curve analysis (FIGS. 3A, 3B and FIG. 9) show that six frequently mutated genes seem predictable using our deep-learning approach; AUC values for serine/threonine protein kinase 11 (STK11), EGFR, FAT atypical cadherin 1 (FAT1), SET binding protein 1 (SETBP1), KRAS and TP53 were between 0.733 and 0.856 (Table 4). Availability of more data for training is expected to substantially improve the performance.

TABLE 4

AUC achieved by the network trained on mutations (with 95% CIs) (n = 62 slides from 59 patients).

| | | Per-slide AUC after aggregation by . . . | |
|---|---|---|---|
| Mutations | Per-tile AUC | . . . average predicted probability | . . . percentage of positively classified tiles |
| STK11 | 0.845 (0.838-0.852) | 0.856 (0.709-0.964) | 0.842 (0.683-0.967) |
| EGFR | 0.754 (0.746-0.761) | 0.826 (0.628-0.979) | 0.782 (0.516-0.979) |
| SETBP1 | 0.785 (0.776-0.794) | 0.775 (0.595-0.931) | 0.752 (0.550-0.927) |
| TP53 | 0.674 (0.666-0.681) | 0.760 (0.626-0.872) | 0.754 (0.627-0.870) |
| FAT1 | 0.739 (0.732-0.746) | 0.750 (0.512-0.940) | 0.750 (0.491-0.946) |
| KRAS | 0.814 (0.807-0.829) | 0.733 (0.580-0.857) | 0.716 (0.552-0.854) |
| KEAP1 | 0.684 (0.670-0.694) | 0.675 (0.466-0.865) | 0.659 (0.440-0.856) |
| LRP1B | 0.640 (0.633-0.647) | 0.656 (0.513-0.797) | 0.657 (0.512-0.799) |
| FAT4 | 0.768 (0.760-0.775) | 0.642 (0.470-0.799) | 0.640 (0.440-0.856) |
| NF1 | 0.714 (0.704-0.723) | 0.640 (0.419-0.845) | 0.632 (0.405-0.845) |

As mentioned earlier, EGFR already has targeted therapies. STK11, also known as liver kinase 1 (LKB1), is a tumor suppressor inactivated in 15-30% of non-small cell lung cancers and is also a potential therapeutic target: it has been reported that phenformin, a mitochondrial inhibitor, increases survival in mice. Also, it has been shown that STK11 mutations in combination with KRAS mutations resulted in more aggressive tumors. FAT1 is an ortholog of the Drosophila fat gene involved in many types of cancers, and its inactivation is suspected to increase cancer cell growth. Mutation of the tumor suppressor gene TP53 is thought to lead to resistance to chemotherapy, resulting in lower survival rates in small-cell lung cancers. Mutation inn SETBP1 like KEAP1 and STK11, has been identified as one of the signatures of LUAD.

Figure 3C:
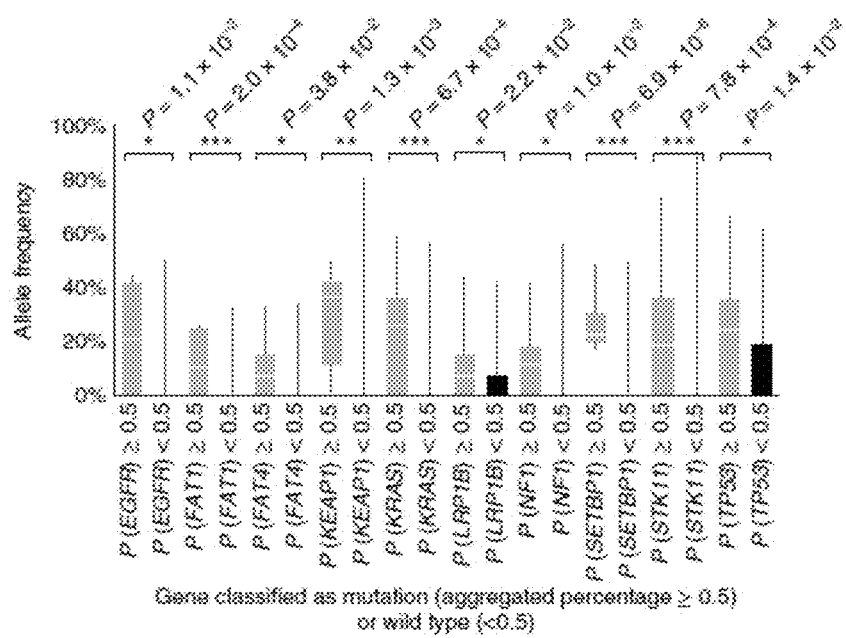
Figure 4A:
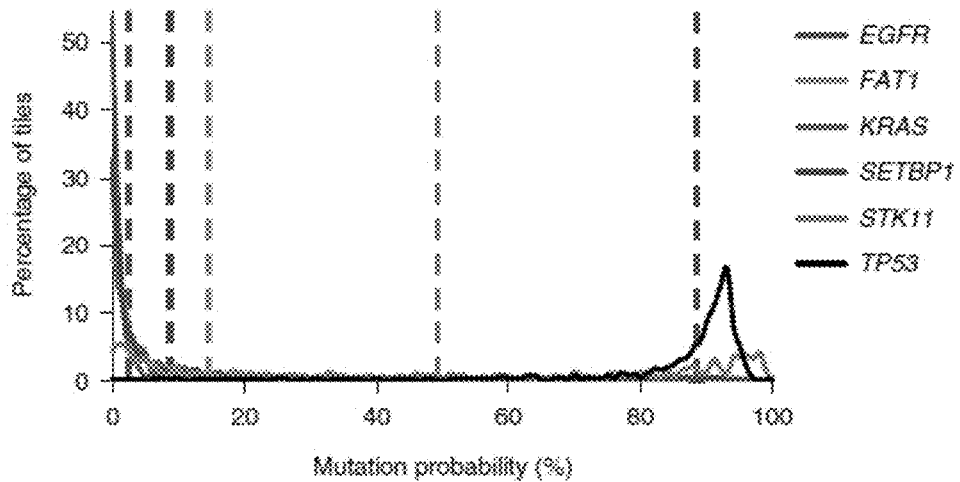
FIGS. 4A-E show spatial heterogeneity of predicted mutations.
Figure 4B:
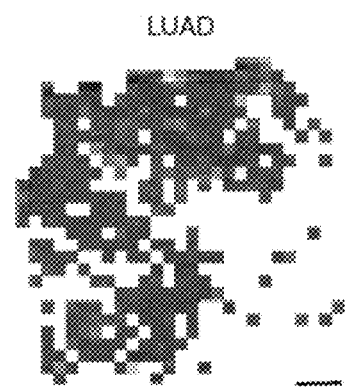
Figure 4C:
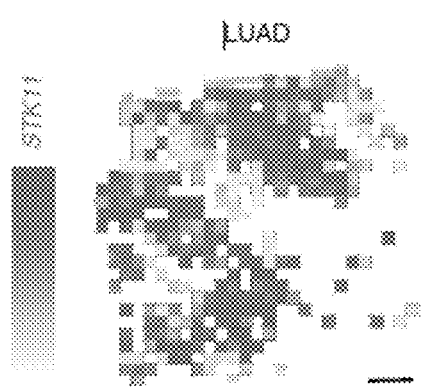
Figure 4D:
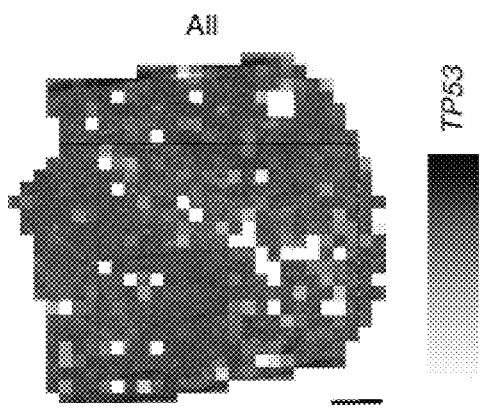
Figure 4E:
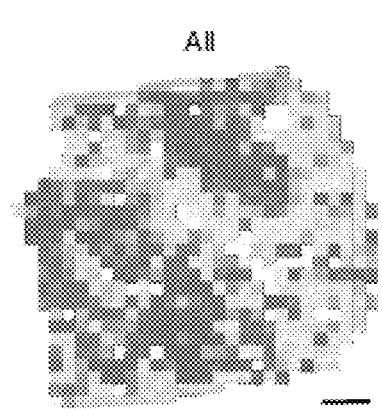

Finally, for each gene, we compared the classification achieved by our deep-learning model with the allele frequency (FIG. 3C). Among the gene mutations predicted with a high AUC, in four of them, classification probabilities (as reported by our model) were associated with allele frequency: FAT1, KRAS, SETBP1, and STK11, demonstrating that these probabilities may reflect the percentage of cells effectively affected by the mutation. Looking, for example, at the predictions performed on the whole-slide image from FIG. 4A, our process successfully identified TP53 (allele frequency of 0.33) and STK11 (allele frequency of 0.25) as the two genes that were most likely mutated (FIG. 4A). The heatmap shows that almost all of the LUAD tiles are highly predicted to show TP53-mutant-like features (FIG. 4B), and two major regions with STK11-mutant-like features (FIG. 4C). Interestingly, when the classification is applied on all tiles, it shows that even tiles classified as LUSC present TP53 mutations (FIG. 4D), whereas the STK11 mutant is confined to the LUAD tiles (FIG. 4E). These results are realistic considering that, as mentioned earlier, STK11 mutation is a signature of LUAD, whereas TP53 mutation is more common in all human cancers. In one embodiment, such as illustrated in FIG. 4A-E, heterogeneity can be a mixture of predicted mutations. The references mapping can be viewed as one or more overlays.

Figure 10A:
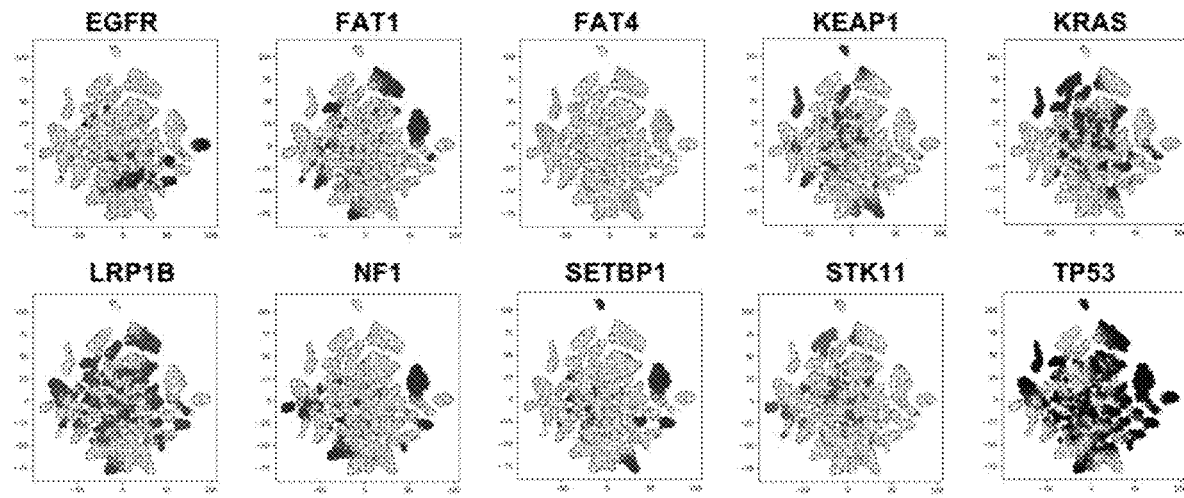
FIGS. 10A-B show illustration of gene mutations learned by deep-learning projected to 2 dimensions for visualization via the t-SNE algorithm using values of the last fully connected layer.
Figure 10B:
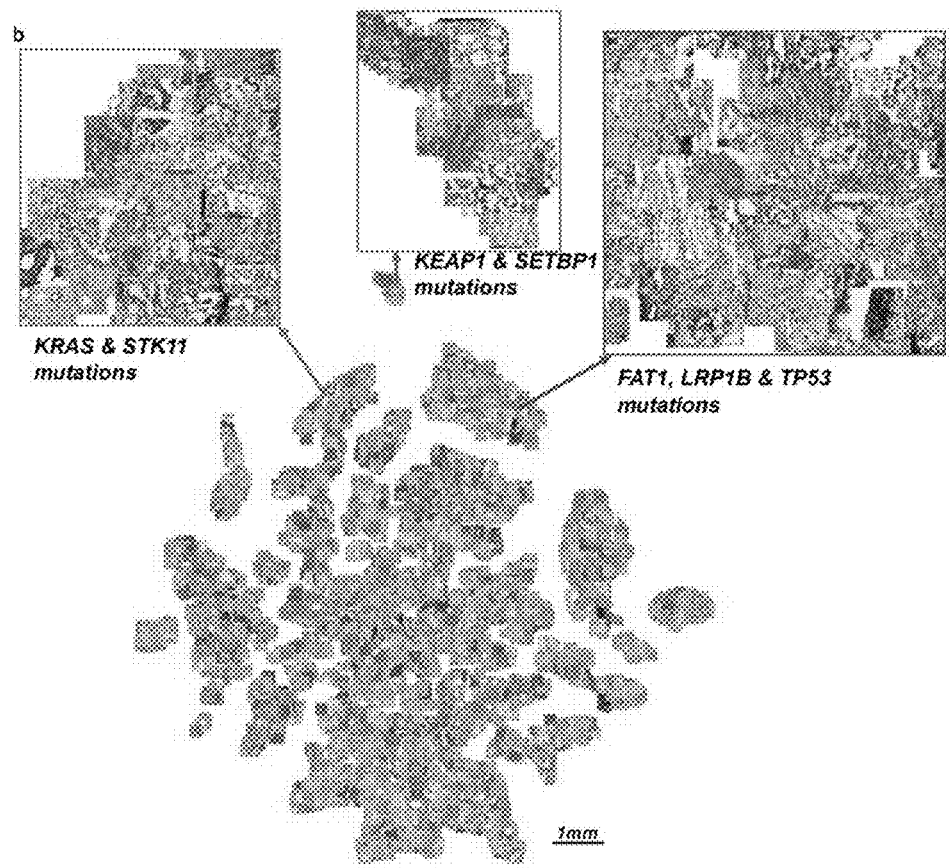

Future work on deep-leaning model visualization tools would help identify and characterize the features used by the neural network. To visualize how the mutations and tiles are organized in the multidimensional space of the network, we used as before a t-SNE representation with the values of the last fully connected layer used an inputs. On the resulting plots (FIG. 10A), each dot represents a tile, and its color is proportional to the probability of the gene to be mutated, as estimated by our model. The tile-embedded representation (FIG. 10B) allows the visual comparison of tiles sharing similar predicted mutations. Clusters of specific mutations can be seen at the surroundings of the plot. The top left group, for example, shows tiles in which the aggressive double mutants KRAS and STK11 are both present, while the small one at the top shows tiles with KEAP1 and SETBP1 mutants and the cluster on the top right has been associated with the triple mutation of FAT1, LRP1B, and TP53. Future analysis with laser-capture microdissection could provide some additional spatial information and could study the limits and precision of such a method.

Although our current analysis does not define the specific features used by the network to identify mutations, our results suggest that such genotype-phenotype correlations are detectable. Determining mutation status from a histological image and bypassing additional testing is important in lung cancer in particular, as these mutations often carry prognostic as well as predictive information. Previous work has shown associations between clinically important mutations and specific patterns of lung adenocarcinoma as well as with the histologic changes that correspond with the evolution of resistance. More recently, Chiang et al. empirically demonstrated the relationship between a defining mutation and the unique morphology of a breast cancer subtype. Some of the mutations with high AUCs highlighted in our study (like those in STK11, TP53 and EGFR) have been shown to affect cell polarity and cell shape, two features that are not routinely assessed during the pathologic diagnosis. We note that our model was not able to detect ALK mutations, although such tumors have been associated with specific histologic features, such as a solid pattern with signet ring cells or a mucinous cribriform pattern. Although the prevalence of ALK mutations is very low (reportedly ranging from 1.8-6.4%), their presence is routinely determined via immunohistochemistry, as tumors with this mutation may respond to ALK inhibitors.

To confirm that our models can be applied to independent cohorts, we tested the prediction of the EGFR mutant using 63 whole-slide images of lung resection specimens with known EGFR mutational status: 29 EGFR mutant and 34 EGFR wild-type samples. This independent dataset has some important differences from the TCGA dataset, which may negatively impact the evaluation of the TCGA-based model: (i) the samples were not frozen but were instead preserved using FFPE, and (ii) only 22 samples had sequencing data to support the EGFR mutational status with high specificity and sensitivity; the rest of the samples (i.e., 65% of the test set) have been analyzed by immunohistochemical (IHC) stains, a technique known for its high specificity but low sensitivity and which solely identifies the two most common mutations (p.L858R and p.E746_A750del). On the other hand, data from the TCGA dataset used for training were identified with the next-generation sequencing (NGS) tools Illumina HiSeq 2000 or Genome Analyzer II. Our TCGA model has therefore been trained to detect not only p.L858R and p.E746 A75-del, but many other EGFR mutants and deletions, such as p.G719A, p.L861Q or p.E709_T710delinsD, for example.

Despite these caveats, we believed that it would still be important to demonstrate that our TCGA-derived models can at least perform significantly better than random in the independent NYU cohort. Indeed, the results showed an AUC of 0.687 (CI, 0.554-0.811), with a higher AUC (0.750; CI, 0.500-0.966) in samples validated by sequencing than in those tested by IHC (AUC, 0.659; CI, 0.485-0.826). Although the sequencing-based AUC of 0.75 is lower than the one estimated on the TCGA test set (0.83), we believe that most of this difference can be attributed to the difference in the sample preparation (frozen versus FFPE). We noticed that the discrepancy (~0.08) is similar to the difference observed in the AUCs of LUAD from the TCGA dataset 0.97) and the FFPE dataset (0.83). In the classification task, this issue was solved by lowering the magnification to 5×. However, this is not useful for the mutation prediction task, because it appears that 20× is necessary to capture predictive image features (the TCGA EGFR mutation prediction model at 5× has a random performance). Still, we believe that the 0.75 AUC we obtained on the sequencing validated subset of EGER-mutant cases demonstrates that the model can generalize on independent datasets.

Experimental Results

Figure 11:
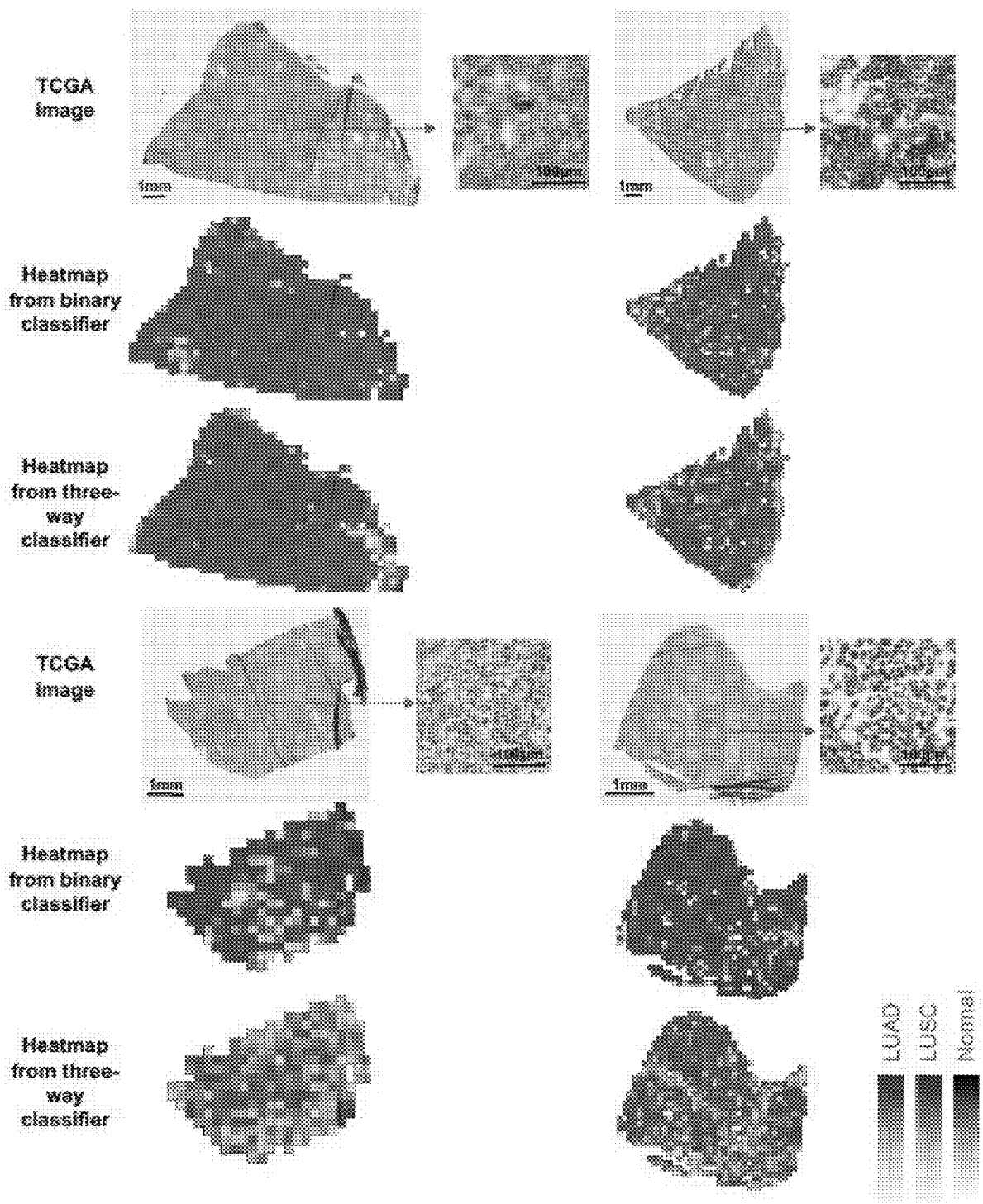
FIG. 11 shows examples of cases classified correctly by the algorithm but misclassified by at least one pathologist. For each case, we show the original image with a 250×250 um zoom from the center of the image, the heatmap generated by the LUAD/LUSC binary classifier and the heatmaps from the Norma/LUAD/LUSC classifier. Training was done once.
Figure 12:
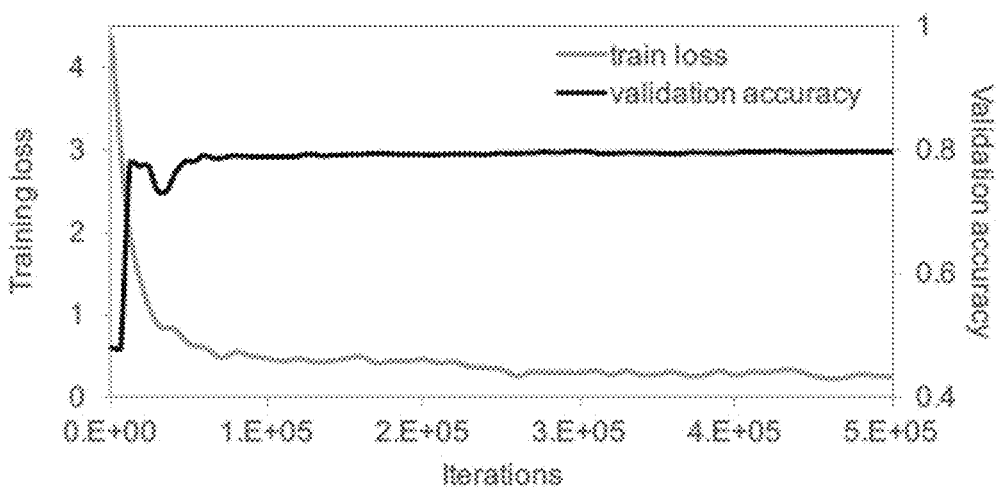
FIG. 12 shows evolution of train loss and validation accuracy during the training of the modified architecture inception v3 for the prediction of mutations. n~212,00) tiles from 320 slides for the training set and n~24,400 tiles from 48 slides for the validation set.
Figures 13A, 13B:
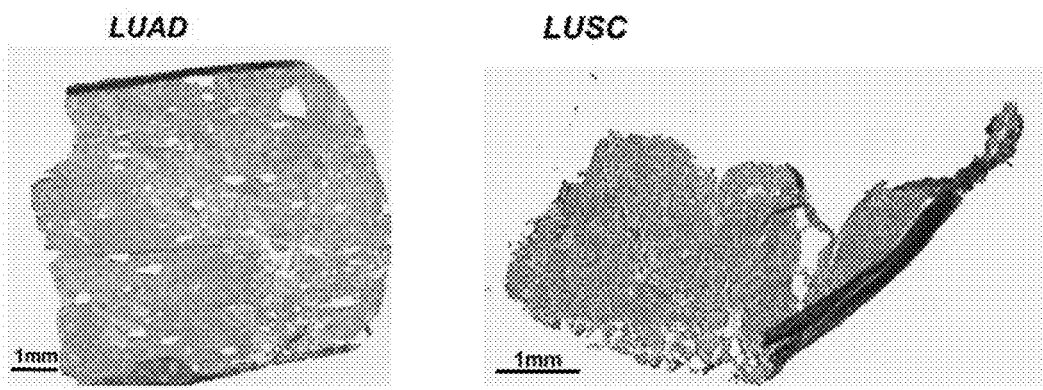
FIGS. 13A-D show heatmaps for classification of Normal vs LUAD vs LUSC.
Figures 13C, 13D:
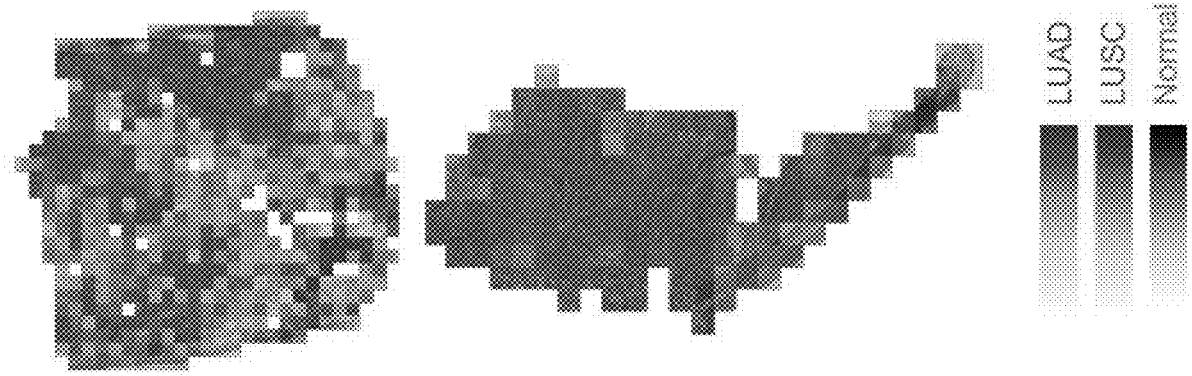
Figure 14A:
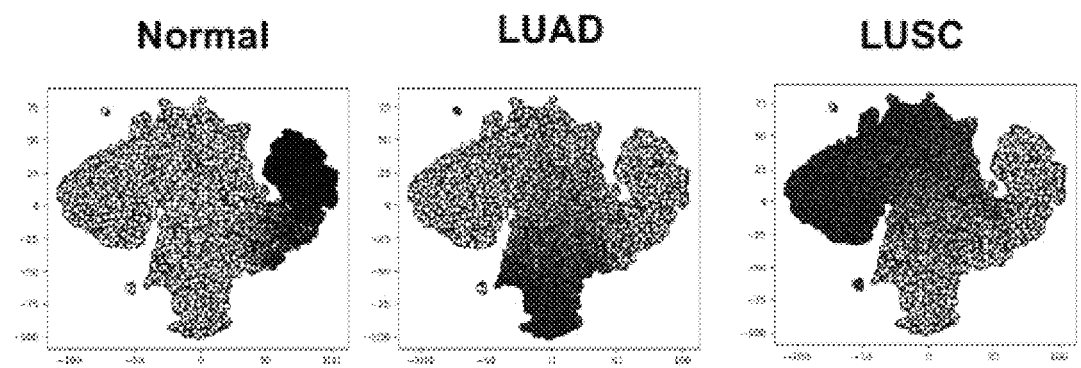
FIGS. 14A-B show illustrations of three-way classifier learned by deep-learning projected to 2 dimensions for visualization via the t-SNE algorithm using values of the last fully connected layer.
Figure 14B:
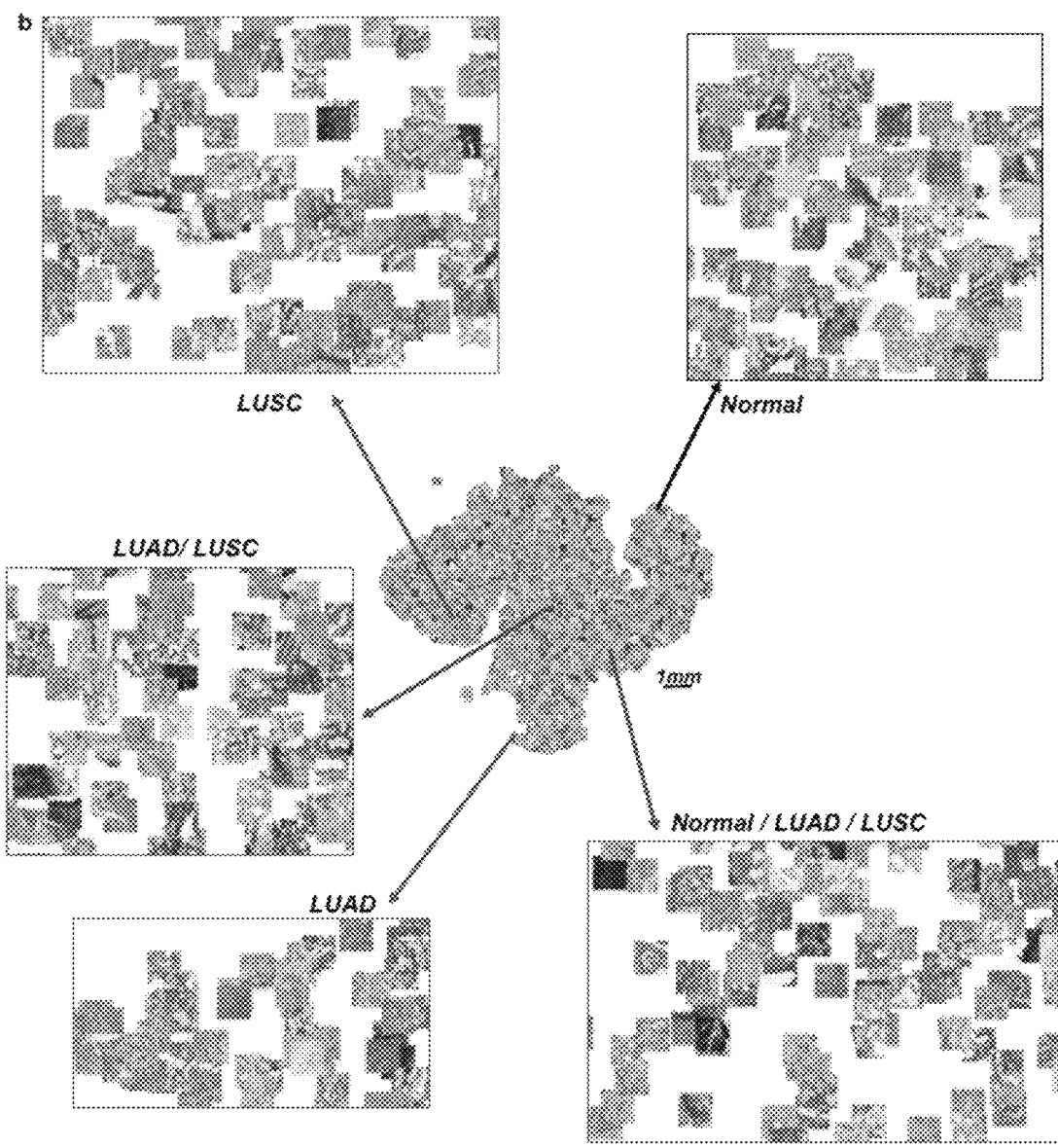

Our study demonstrates that convolutional neural networks, such as Google's inception v3, can be used to assist in the diagnosis of lung cancer from histopathology slides: it almost unambiguously classifies normal versus tumor tissues (~0.99 AUC) and distinguishes lung cancer types with high accuracy (0.97 AUC), reaching sensitivity and specificity comparable to that of a pathologist. Interestingly, around half of the TCGA whole-slide images misclassified by the algorithms have also been misclassified by the pathologists, highlighting the intrinsic difficulty in distinguishing LUAD from LUSC in some cases. However, 45 out of 54 of the TCGA images misclassified by at least one of the pathologists were assigned to the correct cancer type by the algorithm, suggesting that our model could be beneficial in assisting the pathologists in their diagnosis. The confusions matrices in Table 5 detail the discrepancies between the different classifications, and FIG. 11 shows a few examples in which our model correctly classified whole-slide images misclassified by at least one of the pathologists. These images show poorly differentiated tumors that lack the classic histological features of either type (keratinization for LUSC and gland formation/recognizable histological pattern for LUAD). The high accuracy of our model was achieved despite the presence of various artifacts in the TCGA images that were related to sample preparation and preservation procedures.

TABLE 5

Comparison of LUAD/LUSC classifications (number and percentage of cases shown for each confusion matrix; for the LUAD/LUSC classifier, optimal threshold of 0.4/0.6 was selected).

| TCGA dataset | | Pathologist 1 LUAD | Pathologist 1 LUSC | Pathologist 2 LUAD | Pathologist 2 LUSC | Pathologist 3 LUAD | Pathologist 3 LUSC | LUAD/LUSC deep-learning classifier* LUAD | LUAD/LUSC deep-learning classifier* LUSC |
|---|---|---|---|---|---|---|---|---|---|
| TGCA database | LUAD | 72 (42%) | 7 (4%) | 67 (39%) | 12 (7%) | 62 (36%) | 17 (10%) | 73 (43%) | 6 (4%) |
| | LUSC | 21 (13%) | 70 (41%) | 13 (8%) | 78 (46%) | 8 (5%) | 83 (49%) | 9 (5%) | 82 (48%) |
| Pathologist 1 | LUAD | | | 66 (39%) | 27 (16%) | 62 (36%) | 31 (18%) | 72 (42%) | 21 (12%) |
| | LUSC | | | 14 (8%) | 63 (37%) | 8 (5%) | 69 (41%) | 10 (6%) | 67 (40%) |
| Pathologist 2 | LUAD | | | | | 66 (39%) | 13 (8%) | 65 (38%) | 14 (8%) |
| | LUSC | | | | | 5 (3%) | 86 (50%) | 17 (10%) | 74 (44%) |
| Pathologist 3 | LUAD | | | | | | | 59 (35%) | 11 (6%) |
| | LUSC | | | | | | | 23 (14%) | 77 (45%) |

However, the TCGA images used to train the deep neural network may not fully represent the diversity and heterogeneity of tissues that pathologists typically inspect, which may include additional features such as necrosis, blood vessels, and inflammation. More slides containing such features would be needed to retrain the network in order to further improve its performance. Despite this and the fact that the process was trained on frozen images, tests show very promising results on tumor classification from FFPE sections as well. Although it has been suggested that mutations could be predicted from H&E images (AUC of ~0.71 for the prediction of SPOP mutations from prostate cancer H&E images), before this study, it was unclear whether gene mutations would affect the pattern of tumor cells on a lung cancer whole-slide image, but training the network using the presence or absence of mutated genes as a label revealed that there are certain genes whose mutational status can be predicted from image data alone: EGFR, STK11, FAT1, SETBP1, KRAS, and TP53. Notably, the presence of STK11 mutations can be predicted with the highest accuracy (~0.85 AUC). A limiting factor in Obtaining higher accuracies lies in the small number of slides that contain positive instances (i.e., the gene mutations) available for training; therefore, our models can greatly benefit from larger datasets that may become available in the near future. The ability to quickly and inexpensively predict both the type of cancer and the gene mutations from histopathology images could be beneficial to the treatment of patients with cancer given the importance and impact of these mutations.

Overall, this study demonstrates that deep-learning convolutional neural networks could be a very useful tool for assisting pathologists in their classification of whole-slide images of lung tissues. This information can be crucial in applying the appropriate and tailored targeted therapy to patients with lung cancer, increasing thereby the scope and performance of precision medicine that aims at developing a multiplex approach with patient-tailored therapies. The diagnosis and therapy differ considerably between LUSC and LUAD and may depend on the mutational status of specific genes. In particular, when inspecting frozen section biopsies, pathologists only rely on morphology and may need immunostaining for the most difficult cases; our algorithm, which still achieves an AUC above 0.8 on biopsies that usually require immunostaining, can be used as an adjunct to telepathology to speed up diagnosis and classification during intraoperative consultation. As a result of advances in our understanding of lung cancer and a concomitant rise in the number and types of treatment options, the role of the pathologist in the diagnosis and management of this disease is substantially more complex than cancer type distinction and even determination of mutational status. Although our computational analyses may play a role in the initial diagnosis with the benefit of providing important prognostic information based on an H&E image alone, the pathologist has additional tasks, such as staging the tumor and, in an increasing number of cases, estimating response to treatment.

Additional Embodiments

In the future, we would ideally extend the classification to other types of less common lung cancers (large-cell carcinoma, small-cell lung cancer) and histological subtypes of LUAD (acinar, lepidic, papillary, micropapillary, and solid) as well as to non-neoplastic features including necrosis, fibrosis, and other reactive changes in the tumor microenvironment, though the amount of data currently available is insufficient. We hope that by extending our algorithm to recognize a wider range of histologic features, followed by providing a quantitative and spatial assessment as in our heatmaps, we will be able to aid aspects of the pathologists' evaluation that are well-suited to automated analyses. We hope that this computational approach could play a role in both routine tasks and difficult cases (for example, distinguishing intrapulmonary metastases from multiple synchronous primary lung cancers) in order to allow the pathologist to concentrate on higher-level decisions, such as integrating histologic, molecular, and clinical information in order to guide treatment decisions for individual patients.

Figure 15:
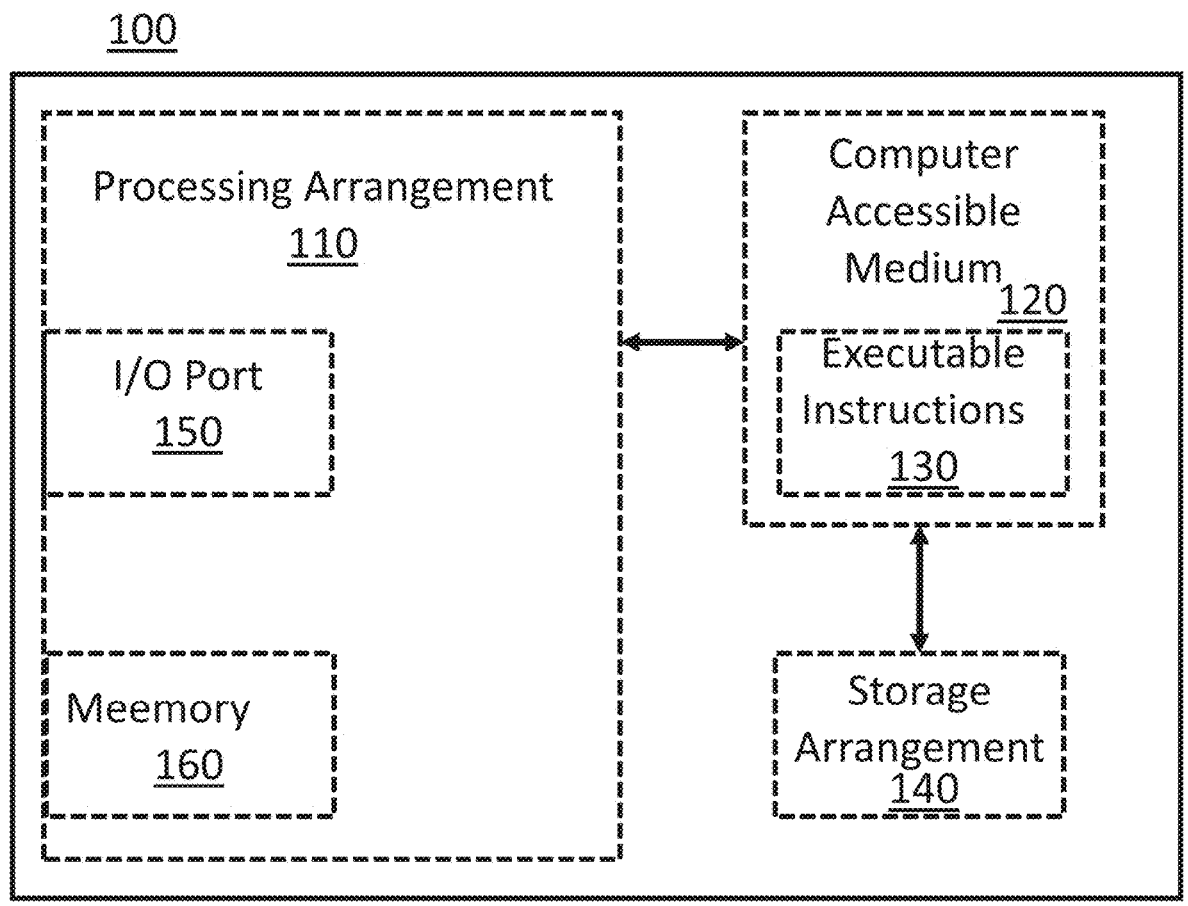
FIG. 15 illustrates a computer system for use with certain implementations.

As shown in FIG. 15, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition, or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example. The instructions may include a plurality of sets of instructions. For example, in some implementations, the instructions may include instructions for applying radio frequency energy in a plurality of sequence blocks to a volume, where each of the sequence blocks includes at least a first stage. The instructions may further include instructions for repeating the first stage successively until magnetization at a beginning of each of the sequence blocks is stable, instructions for concatenating a plurality of imaging segments, which correspond to the plurality of sequence blocks, into a single continuous imaging segment, and instructions for encoding at least one relaxation parameter into the single continuous imaging segment.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding ads for implementing the fundi OM described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

As used herein, the singular forms "a", "an" and "the" include plural referents unless the context clearly dictates otherwise. Thus, for example, the term "a member" is intended to mean a single member or a combination of members. "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method of determining cell genotype comprising:
   obtaining images selected by an automatic tumor selection model of a plurality of cells selected from frozen cells, formalin-fixed paraffin embedded (FFPE) cells, and biopsy cell;
   analyzing the images with a machine learning device;
   determining predicted genotype of the plurality of cells based on the analyzed images; and
   generating a map of spatial heterogeneity based upon the predicted genotype.

2. The method of claim 1, the method further comprising:
   classifying, by the machine learning device, the images into at least one of normal tissue or cancerous tissue based on predicted mutations identified from histopathology data.

3. The method of claim 1, the method further comprising:
   classifying, by the machine learning device, the images into at least one of normal lung tissue, lung adenocarcinoma, or lung squamous cell carcinoma based on predicted mutations identified from histopathology data.

4. The method of claim 1, the method further comprising:
   classifying, by the machine learning device the images into at least one of normal tissue or cancerous tissue with an AUC of greater than 0.95.

5. The method of claim 1, the method further comprising:
   distinguishing, by the machine learning device, between lung adenocarcinoma and lung squamous cell carcinoma with an AUC of greater than 0.95.

6. The method of claim 1, the method further comprising:
   predicting, by the machine learning device, a mutated gene in lung adenocarcinoma, the mutated gene comprising at least one of STK11, EGFR, SETBP1, TP53, FAT1, KRAS, KEAP1, LRP1B, FAT4, or NF1.

7. The method of claim 1, the method further comprising:
   tiling, by the machine learning device, the images into sets of windows of between 75×75 µm to 1000×1000 µm.

8. The method of claim 1, the method further comprising:
   labeling, by the machine learning device, the images using information obtained from at least one of molecular testing or staining.

9. The method of claim 1, wherein the predicted genotype is at least one of normal lung tissue, lung adenocarcinoma, or lung squamous cell carcinoma.

10. The method of claim 1, wherein the plurality of cells are lung cells.

11. The method of claim 1, further comprising:
identifying a course of treatment based on the predicted genotype of the plurality of cells.

12. The method of claim 1, further comprising:
supplementing a pathologist's classification of whole-slide images of lung tissue.

13. A computer-implemented machine for characterizing tumors comprising:
a processor; and
a tangible computer-readable medium operatively connected to the processor and including computer code configured to:
receive image data from a plurality of cells selected by an automatic tumor selection model from frozen cells, formalin-fixed paraffin embedded (FFPE) cells, and biopsy cells associated regarding a region of interest;
tile images into sets of windows of between 75×75 μm to 1000×1000 μm;
analyze each of the windows with a machine learning system to identify phenotypic information for each of the windows;
predict genotypic information for each window from the phenotypic information; and
generate a heatmap for the region of interest based on the predicted genotypic information for each window.

14. The computer-implemented machine of claim 13, wherein the computer code is configured to classify the images into at least one of normal tissue or cancerous tissue.

15. The computer-implemented machine of claim 13, wherein the computer code is configured to classify the images into at least one of normal lung tissue, lung adenocarcinoma, or lung squamous cell carcinoma.

16. The computer-implemented machine of claim 13, wherein the computer code is configured to classify the images into at least one of normal tissue or cancerous tissue with an AUC of greater than 0.95.

17. The computer-implemented machine of claim 13, wherein the computer code is configured to distinguish between lung adenocarcinoma and lung squamous cell carcinoma with an AUC of greater than 0.95.

18. The computer-implemented machine of claim 13, wherein the computer code is configured to predict a mutated gene in lung adenocarcinoma, the mutated gene comprising at least one of STK11, EGFR, SETBP1, TP53, FAT1, KRAS, KEAP1, LRP1B, FAT4, or NF1.

19. The computer-implemented machine of claim 13, wherein the predicted genotypic information is at least one of normal lung tissue, lung adenocarcinoma, or lung squamous cell carcinoma.

20. The computer-implemented machine of claim 13, wherein the computer code is configured to identify a course of treatment based on the predicted genotypic information.

21. A method of determining tumor heteorgenity comprising:
obtaining images of a plurality of cells selected by an automatic tumor selection model from frozen cells, formalin-fixed paraffin embedded (FFPE) cells, and biopsy cells;
analyzing the images with a machine learning device;
determining predicted genotype of the plurality of cells based on the analyzed images; and
generating a heatmap for the region of interest based on the predicted genotypic information for each window.

22. The method of claim 21, wherein the tumor heterogenity is spatial heterogeneity.

23. The method of claim 21, wherein the tumor heterogenity is inter-tumor heterogeneity.

24. The method of claim 21, wherein the tumor heterogenity is intra-tumor heterogeneity.

25. The method of claim 21, wherein the predicted genotypic information is at least one of normal lung tissue, lung adenocarcinoma, or lung squamous cell carcinoma.

* * * * *